United States Patent
Matsunaga et al.

(10) Patent No.: US 7,166,722 B2
(45) Date of Patent: Jan. 23, 2007

(54) N-{2-CHLORO-4-[(6,7-DIMETHOXY-4-QUINOLYL)OXY]PHENYL}-N'-(5-METHYL-3-ISOXAZOLYL)UREA SALT IN CRYSTALLINE FORM

(75) Inventors: Naoki Matsunaga, Gunma-Ken (JP);
Satoshi Yoshida, Gunma-Ken (JP);
Ayako Yoshino, Gunma-Ken (JP);
Tatsuo Nakajima, Gunma-Ken (JP)

(73) Assignee: Kirin Beer Kabushiki Kaisha, Tokyo-To (JP)

( * ) Notice: Subject to any disclaimer, the term of this patent is extended or adjusted under 35 U.S.C. 154(b) by 26 days.

(21) Appl. No.: 10/532,104

(22) PCT Filed: Oct. 21, 2003

(86) PCT No.: PCT/JP03/13439

§ 371 (c)(1),
(2), (4) Date: Apr. 21, 2005

(87) PCT Pub. No.: WO2004/035572

PCT Pub. Date: Apr. 29, 2004

(65) Prior Publication Data

US 2006/0052415 A1    Mar. 9, 2006

(30) Foreign Application Priority Data

Oct. 21, 2002   (JP)   ............................. 2002-306101

(51) Int. Cl.
*C07D 401/12*   (2006.01)
*C07D 401/14*   (2006.01)

(52) U.S. Cl. ...................................... 546/153; 514/312

(58) Field of Classification Search ................ 546/153; 514/312
See application file for complete search history.

(56) References Cited

U.S. PATENT DOCUMENTS 6,821,987 B1 * 11/2004 Kubo et al. .................. 514/312
2004/0132727 A1 * 7/2004 Sakai et al. ............... 514/233.8

FOREIGN PATENT DOCUMENTS

| WO | 99/32106 | 7/1999 |
| WO | 01/47890 | 7/2001 |
| WO | 02/32872 | 4/2002 |
| WO | 02/088110 | 11/2002 |
| WO | WO 2004/060373 | * 7/2004 |

OTHER PUBLICATIONS

Matsunage et al. "N- . . . " CA 140:363009 (2004).*
Brittain "Polymorphism in pharmaceutical solids" Marcel Dekker, p. 27-31 (1999).*

* cited by examiner

*Primary Examiner*—Celia Chang
(74) *Attorney, Agent, or Firm*—Oblon, Spivak, McClelland, Maier & Neustadt, P.C.

(57) ABSTRACT

The present invention provides a crystal of a pharmaceutically acceptable salt of N-{2-chloro-4-[(6,7-dimethoxy-4-quinolyl)oxy]phenyl}-N'-(5-methyl-3-isoxazolyl) urea. This crystal of salt is usable for the therapy of a disease selected from the group consisting of tumors, diabetic retinopathy, chronic rheumatism, psoriasis, atherosclerosis, Kaposi's sarcoma, and exudation type age-related maculopathy, and has characteristics suitable for applications of oral pharmaceutical preparations.

16 Claims, 19 Drawing Sheets

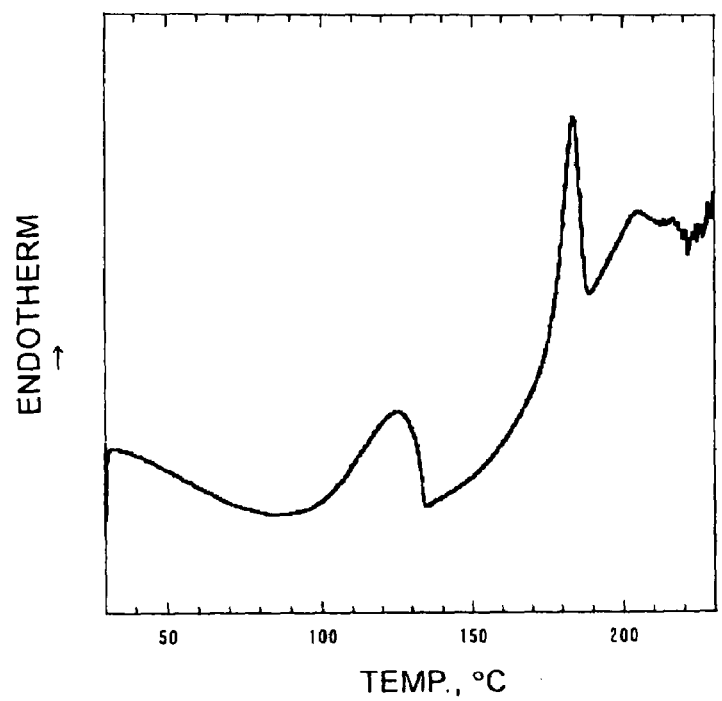
F I G. 27
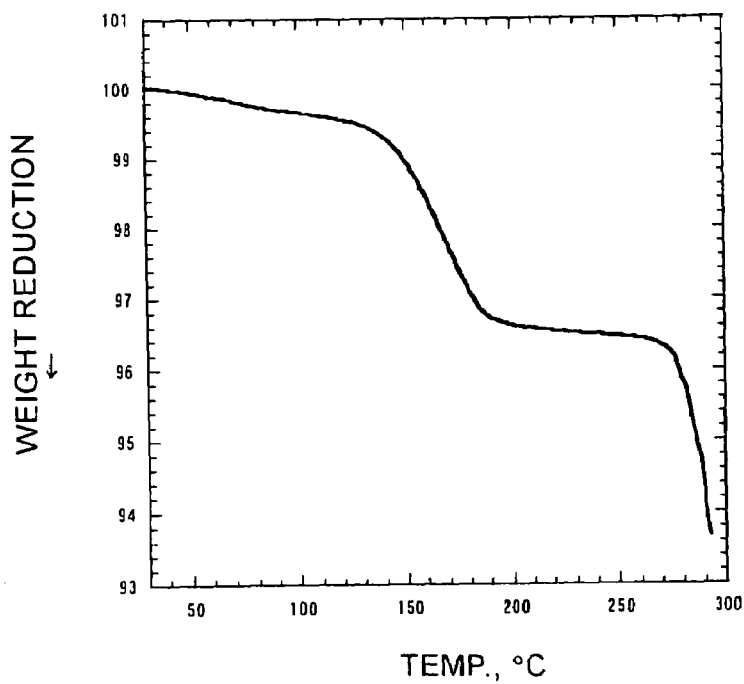
F I G. 28

N-{2-CHLORO-4-[(6,7-DIMETHOXY-4-QUINOLYL)OXY]PHENYL}-N'-(5-METHYL-3-ISOXAZOLYL)UREA SALT IN CRYSTALLINE FORM

BACKGROUND OF THE INVENTION

1. Field of the Invention

The present invention relates to crystals of pharmaceutically acceptable salts of N-{2-chloro-4-[(6,7-dimethoxy-4-quinolyl)oxy]phenyl}-N'-(5-methyl-3-isoxazolyl)urea and a process for producing the same.

2. Related Art

In the field of research in the therapy of diseases such as tumors, diabetic retinopathy, chronic rheumatism, psoriasis, atherosclerosis, and Kaposi's sarcoma, a number of drugs have been used clinically through various approaches. Medical treatment with chemotherapeutics, however, has posed problems of side effects of drugs, individual differences in patients and the like. This has led to a demand for better drugs. Further, when QOL (quality of life) of patients is taken into consideration, an increase in diversification of dosage forms of drugs is demanded.

For example, in formulation into tablets, capsules, powders, granules, and suspensions for oral administration, or formulation into suppositories, tapes, and ointments for parenteral administration, original drugs should satisfy requirements for preparations as pharmaceuticals, that is, should have physicochemical properties that can realize prescription which satisfies prescribed quality and development of efficacy. Further, the original drug as a pharmaceutical should be produced by a process that can realize stable production of the original drug on a commercial scale and is suitable for mass production on a commercial scale.

SUMMARY OF THE INVENTION

The present inventors have found that N-{2-chloro-4-[(6,7-dimethoxy-4-quinolyl)oxy]phenyl}-N'-(5-methyl-3-isoxazolyl)urea is effective in the therapy of diseases such as tumors, diabetic retinopathy, chronic rheumatism, psoriasis, atherosclerosis, and Kaposi's sarcoma. The present inventors have previously filed an application (an application under PCT (PCT/JP02/04279, WO02/88110)) concerning this compound and a synthetic process thereof. In this application, however, there is no description about crystalline forms of salts of the compound and a production process thereof.

The present inventors have now found that, in the crystalline form of salts of N-{2-chloro-4-[(6,7-dimethoxy-4-quinolyl)oxy]phenyl}-N'-(5-methyl-3-isoxazolyl)urea, there exist a plurality of polymorphs that are different from each other or one another in various physicochemical properties. The present inventors have further found that some crystal polymorphs have properties required of pharmaceutical preparations for oral administration, that is, are stable against thermal stress and physical stress and stable under high humidity conditions, that is, have a low level of hygroscopicity. The present inventors have also found a production process that can stably supply some of the crystals of salts of N-{2-chloro-4-[(6,7-dimethoxy-4-quinolyl)oxy]phenyl}-N'-(5-methyl-3-isoxazolyl)urea and can also be applied to commercial scale production. The present invention has been made based on such finding.

Accordingly, an object of the present invention is to provide crystals that are crystals of salts of N-{2-chloro-4-[(6,7-dimethoxy-4-quinolyl)oxy]phenyl}-N'-(5-methyl-3-isoxazolyl)urea and have properties suitable for applications of pharmaceutical preparations for oral administration.

The crystal of a salt according to the present invention is a crystal of a pharmaceutically acceptable salt of N-{2-chloro-4-[(6,7-dimethoxy-4-quinolyl)oxy]phenyl}-N'-(5-methyl-3-isoxazolyl)urea.

In the present invention, the crystal of a preferred salt is selected from the group consisting of form I crystal of hydrochloride, form II crystal of hydrochloride, form I crystal of p-toluenesulfonate, form II crystal of p-toluenesulfonate, and form II crystal of maleate of N-{2-chloro-4-[(6,7-dimethoxy-4-quinolyl)oxy]phenyl}-N'-(5-methyl-3-isoxazolyl)urea.

The crystal of a salt according to the present invention is useful for the therapy of a disease selected from the group consisting of tumors, diabetic retinopathy, chronic rheumatism, psoriasis, atherosclerosis, Kaposi's sarcoma, and exudation type age-related maculopathy.

BRIEF DESCRIPTION OF THE DRAWINGS

FIG. 27 is a differential scanning calorimetrically measured chart of form II crystal of p-toluenesulfonate prepared in Example 14;

FIG. 28 is a thermogravimetrically measured chart of form II crystal of p-toluenesulfonate prepared in Example 14;

DETAILED DESCRIPTION OF THE INVENTION

Figure 1:
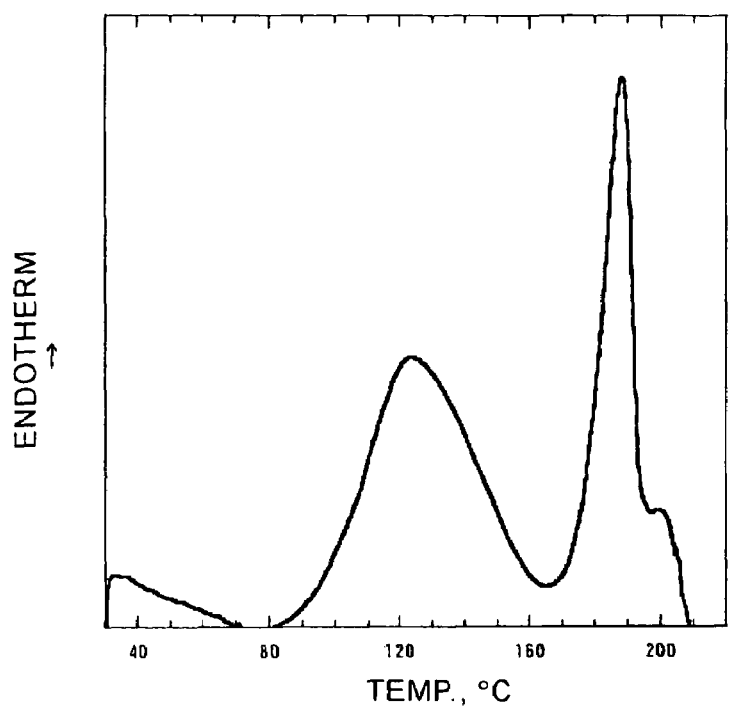
FIG. 1 is a differential scanning calorimetrically measured chart of form I crystal of hydrochloride prepared in Example 1.

Crystal of Salt According to the Invention

As described above, the crystal of salt according to the present invention is a crystal of a pharmaceutically acceptable salt of N-{2-chloro-4-[(6,7-dimethoxy-4-quinolyl)oxy]phenyl}-N'-(5-methyl-3-isoxazolyl)urea. The crystal according to the present invention is preferably suitable for oral pharmaceutical preparations.

The expression "pharmaceutically acceptable salt" as used herein refers to a salt that is suitable for use as pharmaceutical preparations and is basically harmless to organisms. Such pharmaceutically acceptable salts include those derived from pharmaceutically acceptable inorganic acids or organic acids, that is, inorganic acid salts or organic acid salts. Examples of suitable acids include hydrochloric acid, sulfuric acid, nitric acid, perchloric acid, hydrobromic acid, fumaric acid, maleic acid, phosphoric acid, glycolic acid, lactic acid, salicylic acid, succinic acid, p-toluenesulfonic acid, di-p-toluoyl tartaric acid, sulfanilic acid, tartaric acid, acetic acid, citric acid, methanesulfonic acid, formic acid, benzoic acid, malonic acid, naphthalene-2-sulfonic acid, and benzene sulfonic acid. Further, in the present invention, the above-described salts include hydrates, alcoholates, and etherates.

In the present invention, the salt of N-{2-chloro-4-[(6,7-dimethoxy-4-quinolyl)oxy]phenyl}-N'-(5-methyl-3-isoxazolyl)urea is preferably selected from the group consisting of hydrochlorides, nitrates, sulfates, methanesulfonates, p-toluenesulfonates, and maleates of the compound.

For each of hydrochlorides, nitrates, sulfates, methanesulfonates, p-toluenesulfonates, and maleates of N-{2-chloro-4-[(6,7-dimethoxy-4-quinolyl)oxy]phenyl}-N'-(5-methyl-3-isoxazolyl)urea, there exist a few crystal polymorphisms. Crystals of salts according to the present invention are preferably crystals of these salts. Crystals of salts of N-{2-chloro-4-[(6,7-dimethoxy-4-quinolyl)oxy]phenyl}-N'-(5-methyl-3-isoxazolyl)urea may be produced, for example, by any of the methods described in Examples 1 to 19 which will be described later.

Crystal of Hydrochloride

The hydrochloride of N-{2-chloro-4-[(6,7-dimethoxy-4-quinolyl)oxy]phenyl}-N'-(5-methyl-3-isoxazolyl)urea may take crystalline form I, II, or III.

Form I Crystal of Hydrochloride

Form I crystal of N-{2-chloro-4-[(6,7-dimethoxy-4-quinolyl)oxy]phenyl}-N'-(5-methyl-3-isoxazolyl)urea hydrochloride is hydrochloric acid monoadduct and monohydrate (monohydrochloride monohydrate). For form I crystal of the hydrochloride, in the differential scanning calorimetry, an endothermic peak was observed at a temperature around 120° C.; in the thermogravimetry, a 3.7% weight reduction was observed between 100° C. and 160° C.; and, in the water content measurement, the water content was found to be 3.7%. Based on these results, the crystal was determined to be monohydrate.

Accordingly, in one preferred embodiment of the present invention, the crystal of the salt according to the present invention is a crystal of N-{2-chloro-4-[(6,7-dimethoxy-4-quinolyl)oxy]phenyl}-N'-(5-methyl-3-isoxazolyl)urea hydrochloride. More preferably, the crystal of this salt is a crystal of hydrochloric acid monoadduct and monohydrate. Still more preferably, this crystal is form I crystal of hydrochloride.

Form I crystal of N-{2-chloro-4-[(6,7-dimethoxy-4-quinolyl)oxy]phenyl}-N'-(5-methyl-3-isoxazolyl)urea hydrochloride may be produced by the method described in Example 1. The form I crystal of the hydrochloride thus obtained has a powder X-ray diffraction pattern as shown in Table 1 in Example 1.

Accordingly, in one preferred embodiment of the present invention, the crystal of the salt according to the present invention is such that the salt is hydrochloric acid monoadduct and monohydrate and, in powder X-ray diffractometry, the salt has peaks with not less than 10% relative intensity at diffraction angles (2θ) shown in Table A-1 below. More preferably, the relative intensity at the above diffraction angles (2θ) is not less than 15%, more preferably not less than 20%, still more preferably not less than 25%, particularly preferably not less than 30%.

TABLE A-1

| Diffraction angle (2θ) |
|---|
| 11.47 ± X |
| 22.59 ± X |
| 23.02 ± X |
| 26.27 ± X |
| 26.63 ± X | wherein X is 0 to 0.20.

In diffraction angle (2θ) values, errors sometimes occur, for example, attributable to the purity of crystal in powder applied to the powder X-ray diffraction analysis, particle size of the powder, the water content of the powder, an error derived from measurement limit of the powder X-ray diffraction apparatus and the like. In this specification, when the crystal is specified by using diffraction angles 2θ, the diffraction angle 2θ values are not limited to the measured values per se indicated as having peaks in the column of the Examples and an error range is also embraced as diffraction angle 2θ values in the crystal according to the present invention. Typically, the error range is a predetermined value ±0 to 0.02. Therefore, as shown in Table A-1 above, when the diffraction angle 2θ values of the crystal are expressed by X, X is typically 0 to 0.20, preferably 0 to 0.15, more preferably 0 to 0.10, still more preferably 0 to 0.05. These are true of crystals, which will be described later, other than crystals of hydrochloride, for example, crystals of nitrate, sulfate, methanesulfonate, and p-toluenesulfonate.

In a more preferred embodiment of the present invention, the crystal of the salt according to the present invention is such that the salt is hydrochloric acid monoadduct and monohydrate and, in powder X-ray diffractometry, the salt has peaks with not less than 10% relative intensity at diffraction angles (2θ) shown in Table B-1 below. More preferably, the relative intensity at the above diffraction angles (2θ) is not less than 15%, more preferably not less than 20%.

TABLE B-1

| Diffraction angle (2θ) |
|---|
| 8.76 ± X |
| 11.47 ± X |
| 15.28 ± X |
| 17.16 ± X |
| 17.53 ± X |
| 18.80 ± X |
| 20.02 ± X |
| 22.59 ± X |
| 23.02 ± X |
| 25.32 ± X |
| 25.43 ± X |
| 26.27 ± X |
| 26.63 ± X |
| 27.00 ± X |
| 28.57 ± X | wherein X is 0 to 0.20, preferably 0 to 0.15, more preferably 0 to 0.10, still more preferably 0 to 0.05.

Figure 2:
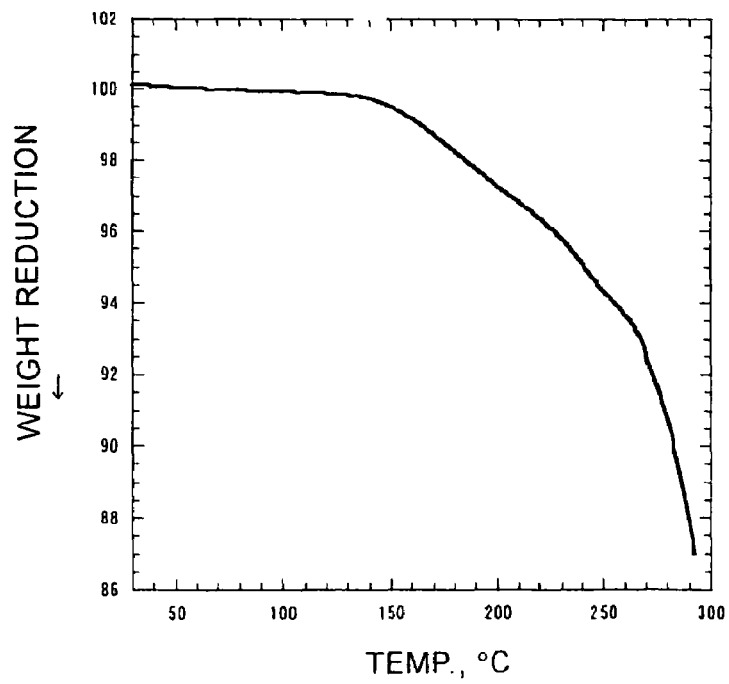
FIG. 2 is a thermogravimetrically measured chart of form I crystal of hydrochloride prepared in Example 1.

Further, form I crystal of the hydrochloride exhibits a differential scanning calorimetrically measured (DSC) chart as shown in FIG. 1 in which endothermic peaks exist at temperatures around 120° C. and 190° C. Furthermore, form I crystal of the hydrochloride exhibits a thermogravimetrically measured chart as shown in FIG. 2. Form I crystal of the hydrochloride according to the present invention typically has the above features.

Form II Crystal of Hydrochloride

Form II crystal of N-{2-chloro-4-[(6,7-dimethoxy-4-quinolyl)oxy]phenyl}-N'-(5-methyl-3-isoxazolyl)urea hydrochloride is hydrochloric acid monoadduct (monohydrochloride).

Accordingly, in one preferred embodiment of the present invention, the crystal of the salt according to the present invention is a crystal of hydrochloric acid monoadduct. More preferably, this crystal is form II crystal of hydrochloride.

Form II crystal of N-{2-chloro-4-[(6,7-dimethoxy-4-quinolyl)oxy]phenyl}-N'-(5-methyl-3-isoxazolyl)urea hydrochloride may be produced by the method described in Example 2. The form II crystal of the hydrochloride thus obtained has a powder X-ray diffraction pattern as shown in Table 2 in Example 2.

Accordingly, in one preferred embodiment of the present invention, the crystal of the salt according to the present invention is such that the salt is hydrochloric acid monoadduct and, in powder X-ray diffractometry, the salt has peaks with not less than 10% relative intensity at diffraction angles (2θ) shown in Table A-2 below. More preferably, the relative intensity at the above diffraction angles (2θ) is not less than 15%, more preferably not less than 20%, still more preferably not less than 25%, particularly preferably not less than 30%.

TABLE A-2

| Diffraction angle (2θ) |
|---|
| 12.15 ± X |
| 12.54 ± X |
| 21.32 ± X |
| 21.48 ± X |
| 22.13 ± X |
| 24.12 ± X |
| 25.22 ± X |
| 25.95 ± X | wherein X is 0 to 0.20, preferably 0 to 0.15, more preferably 0 to 0.10, still more preferably 0 to 0.05.

In a more preferred embodiment of the present invention, the crystal of the salt according to the present invention is such that the salt is hydrochloric acid monoadduct and, in powder X-ray diffractometry, the salt has peaks with not less than 10% relative intensity at diffraction angles (2θ) shown in Table B-2 below. More preferably, the relative intensity at the above diffraction angles (2θ) is not less than 15%, more preferably not less than 20%.

TABLE B-2

| Diffraction angle (2θ) |
|---|
| 9.37 ± X |
| 12.15 ± X |
| 12.54 ± X |
| 12.88 ± X |
| 21.32 ± X |
| 21.48 ± X |
| 21.82 ± X |
| 22.13 ± X |
| 23.16 ± X |
| 24.12 ± X |
| 25.22 ± X |
| 25.95 ± X | wherein X is 0 to 0.20, preferably 0 to 0.15, more preferably 0 to 0.10, still more preferably 0 to 0.05.

Figure 3:
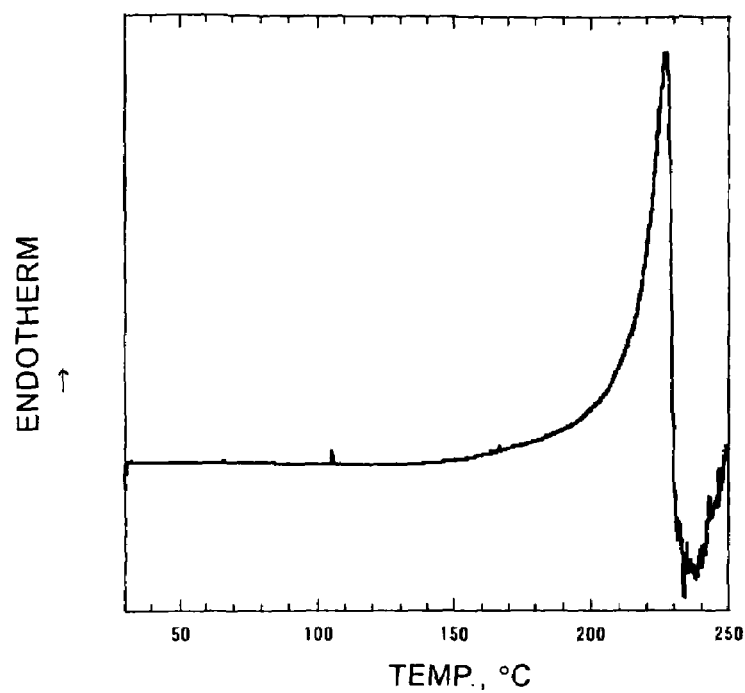
FIG. 3 is a differential scanning calorimetrically measured chart of form II crystal of hydrochloride prepared in Example 2.
Figure 4:
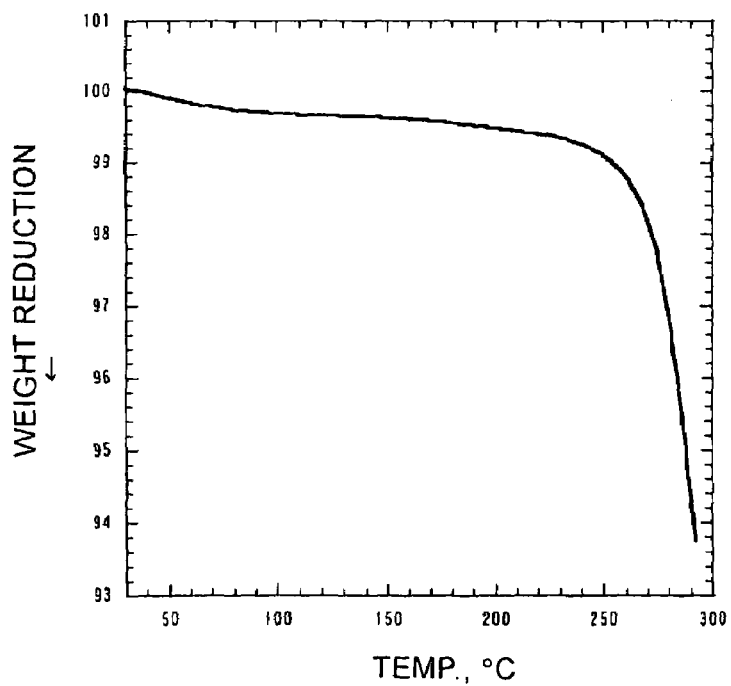
FIG. 4 is a thermogravimetrically measured chart of form II crystal of hydrochloride prepared in Example 2.

Further, form II crystal of the hydrochloride exhibits a differential scanning calorimetrically measured chart as shown in FIG. 3 in which an endothermic peak exists at a temperature around 220° C. Furthermore, form II crystal of the hydrochloride exhibits a thermogravimetrically measured chart as shown in FIG. 4. Form II crystal of the hydrochloride according to the present invention typically has the above features.

Form III Crystal of Hydrochloride

Form III crystal of N-{2-chloro-4-[(6,7-dimethoxy-4-quinolyl)oxy]phenyl}-N'-(5-methyl-3-isoxazolyl)urea hydrochloride is monohydrochloride.

Figure 5:
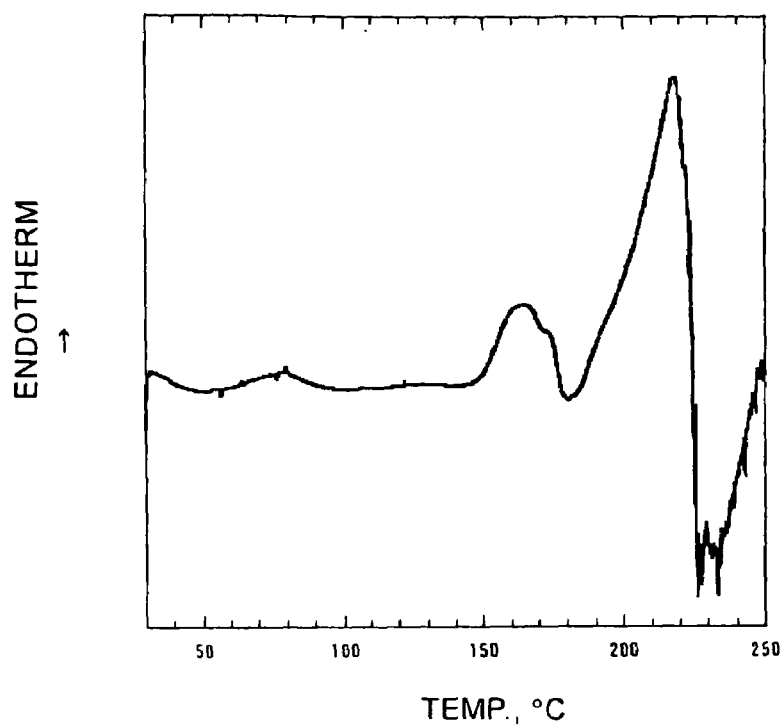
FIG. 5 is a differential scanning calorimetrically measured chart of form III crystal of hydrochloride prepared in Example 3.
Figure 6:
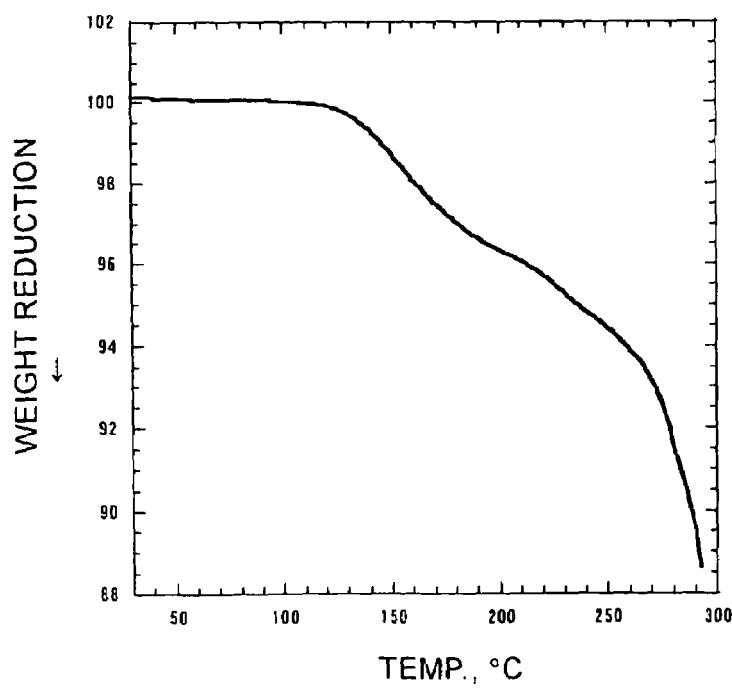
FIG. 6 is a thermogravimetrically measured chart of form III crystal of hydrochloride prepared in Example 3.

Form III crystal of N-{2-chloro-4-[(6,7-dimethoxy-4-quinolyl)oxy]phenyl}-N'-(5-methyl-3-isoxazolyl)urea hydrochloride may be produced by the method described in Example 3. The form III crystal of hydrochloride thus obtained exhibits a powder X-ray diffraction pattern as shown in Table 3 in Example 3. Further, form III crystal of the hydrochloride exhibits a differential scanning calorimetrically measured chart as shown in FIG. 5 in which endothermic peaks exist at temperatures around 160° C. and 220° C. Furthermore, form III crystal of the hydrochloride exhibits a thermogravimetrically measured chart as shown in FIG. 6. Form III crystal of the hydrochloride according to the present invention typically has the above features.

Crystal of Nitrate

The nitrate of N-{2-chloro-4-[(6,7-dimethoxy-4-quinolyl)oxy]phenyl}-N'-(5-methyl-3-isoxazolyl)urea may take crystalline form I or II.

Form I Crystal of Nitrate

Form I crystal of N-{2-chloro-4-[(6,7-dimethoxy-4-quinolyl)oxy]phenyl}-N'-(5-methyl-3-isoxazolyl)urea nitrate is mononitrate.

Figure 7:
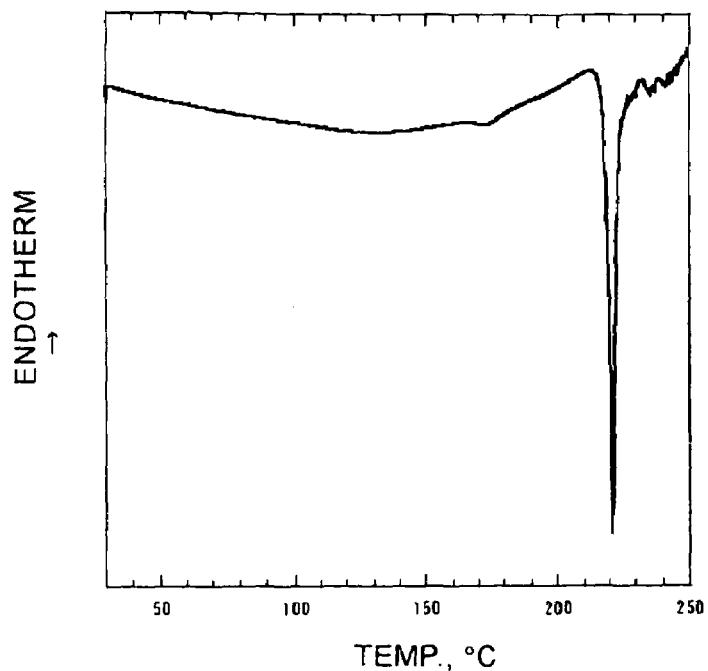
FIG. 7 is a differential scanning calorimetrically measured chart of form I crystal of nitrate prepared in Example 4.
Figure 8:
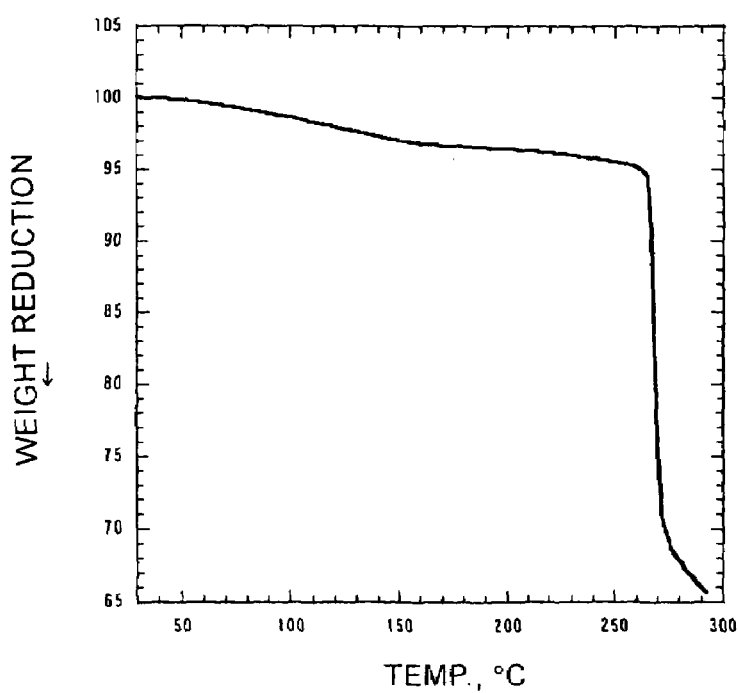
FIG. 8 is a thermogravimetrically measured chart of form I crystal of nitrate prepared in Example 4.

Form I crystal of N-{2-chloro-4-[(6,7-dimethoxy-4-quinolyl)oxy]phenyl}-N'-(5-methyl-3-isoxazolyl)urea nitrate may be produced by the method described in Example 4. The form I crystal of nitrate thus obtained exhibits a powder X-ray diffraction pattern as shown in Table 4 in Example 4. Further, form I crystal of the nitrate exhibits a differential scanning calorimetrically measured chart as shown in FIG. 7 in which an exothermic peak exists at a temperature around 220° C. Furthermore, form I crystal of the nitrate exhibits a thermogravimetrically measured chart as shown in FIG. 8. Form I crystal of the nitrate according to the present invention typically has the above features.

Form II Crystal of Nitrate

Form II crystal of N-{2-chloro-4-[(6,7-dimethoxy-4-quinolyl)oxy]phenyl}-N'-(5-methyl-3-isoxazolyl)urea nitrate is mononitrate.

Figure 9:
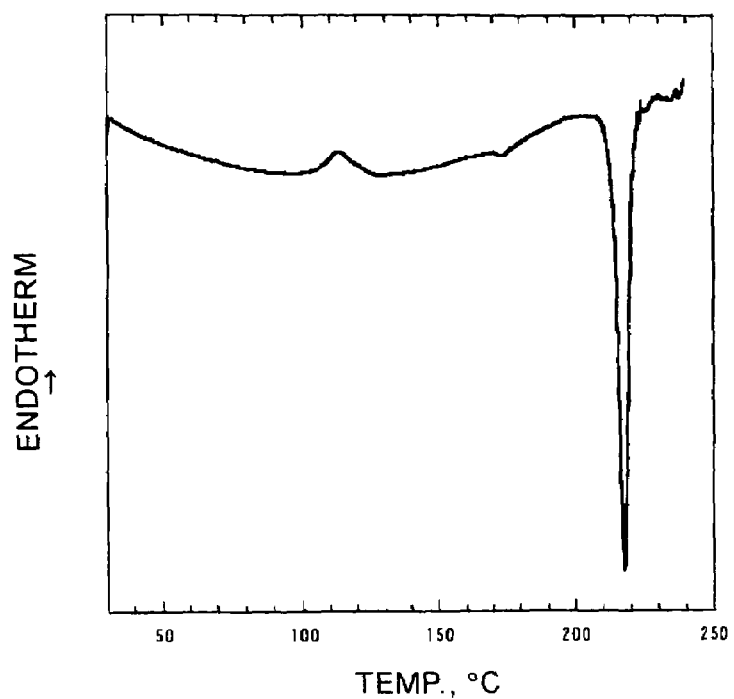
FIG. 9 is a differential scanning calorimetrically measured chart of form I crystal of nitrate prepared in Example 5.
Figure 10:
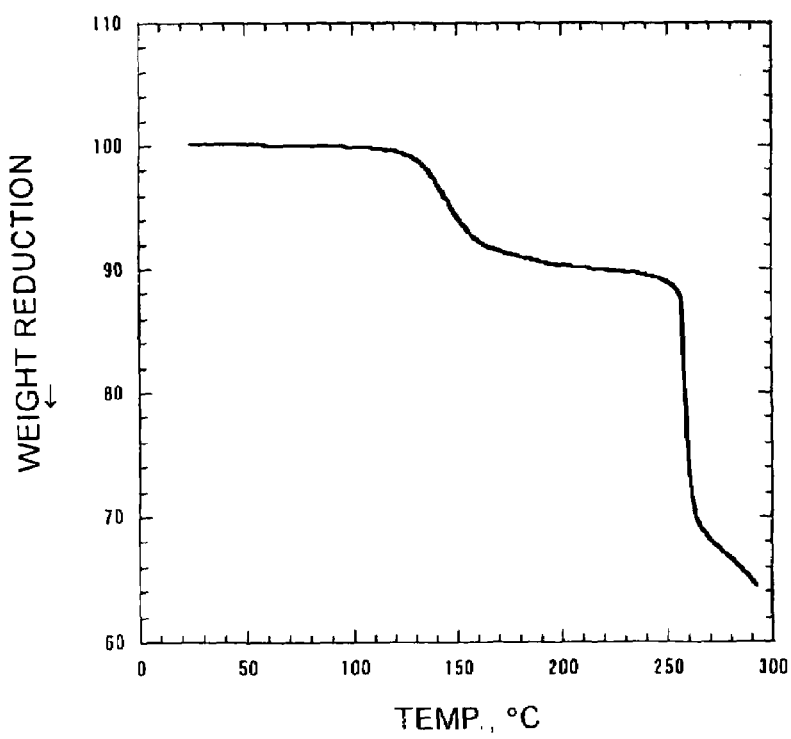
FIG. 10 is a thermogravimetrically measured chart of form II crystal of nitrate prepared in Example 5.

Form II crystal of N-{2-chloro-4-[(6,7-dimethoxy-4-quinolyl)oxy]phenyl}-N'-(5-methyl-3-isoxazolyl)urea nitrate may be produced by the method described in Example 5. The form II crystal of nitrate thus obtained exhibits a powder X-ray diffraction pattern as shown in Table 5 in Example 5. Further, form II crystal of the nitrate exhibits a differential scanning calorimetrically measured chart as shown in FIG. 9 in which an endothermic peak exists at a temperature around 120° C. and an exothermic peak at a temperature around 220° C. Furthermore, form II crystal of the nitrate exhibits a thermogravimetrically measured chart as shown in FIG. 10. Form II crystal of the nitrate according to the present invention typically has the above features.

Crystal of Sulfate

Sulfate of N-{2-chloro-4-[(6,7-dimethoxy-4-quinolyl)oxy]phenyl}-N'-(5-methyl-3-isoxazolyl)urea may take crystalline form I or II.

Form I Crystal of Sulfate

Form I crystal of N-{2-chloro-4-[(6,7-dimethoxy-4-quinolyl)oxy]phenyl}-N'-(5-methyl-3-isoxazolyl)urea sulfate is monosulfate.

Figure 11:
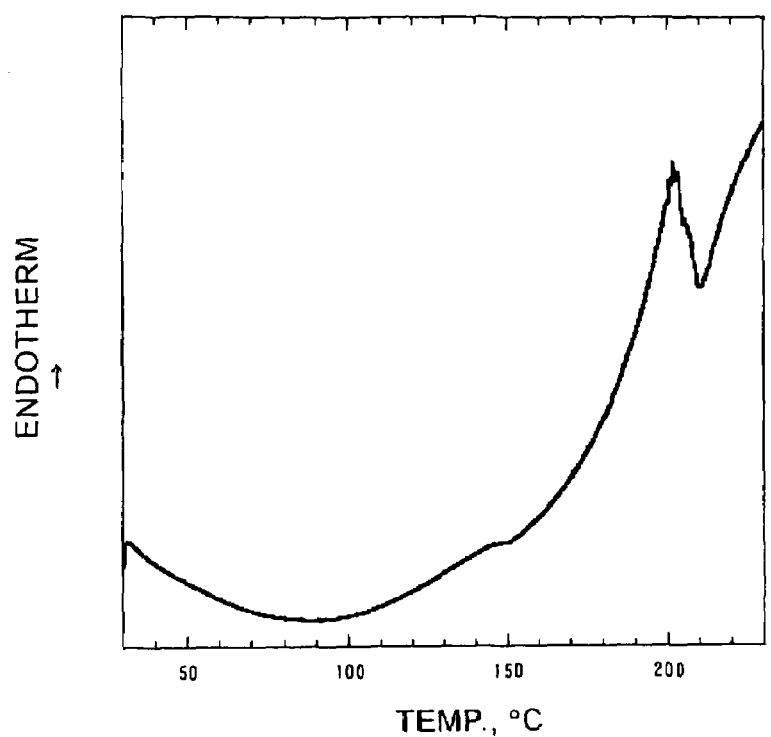
FIG. 11 is a differential scanning calorimetrically measured chart of form I crystal of sulfate prepared in Example 6.
Figure 12:
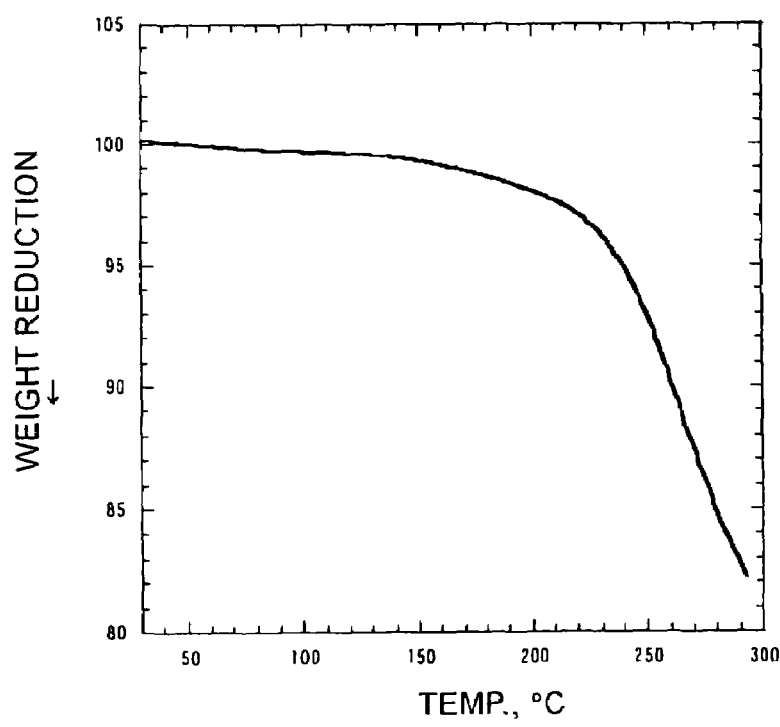
FIG. 12 is a thermogravimetrically measured chart of form I crystal of sulfate prepared in Example 6.

Form I crystal of N-{2-chloro-4-[(6,7-dimethoxy-4-quinolyl)oxy]phenyl}-N'-(5-methyl-3-isoxazolyl)urea sulfate may be produced by the method described in Example 6. The form I crystal of sulfate thus obtained exhibits a powder X-ray diffraction pattern as shown in Table 6 in Example 6. Further, form I crystal of the sulfate exhibits a differential scanning calorimetrically measured chart as shown in FIG. 11 in which an endothermic peak exists at a temperature around 200° C. Furthermore, form I crystal of the sulfate exhibits a thermogravimetrically measured chart as shown in FIG. 12. Form I crystal of the sulfate according to the present invention typically has the above features.

Form II Crystal of Sulfate

Form II crystal of N-{2-chloro-4-[(6,7-dimethoxy-4-quinolyl)oxy]phenyl}-N'-(5-methyl-3-isoxazolyl)urea sulfate is monosulfate.

Figure 13:
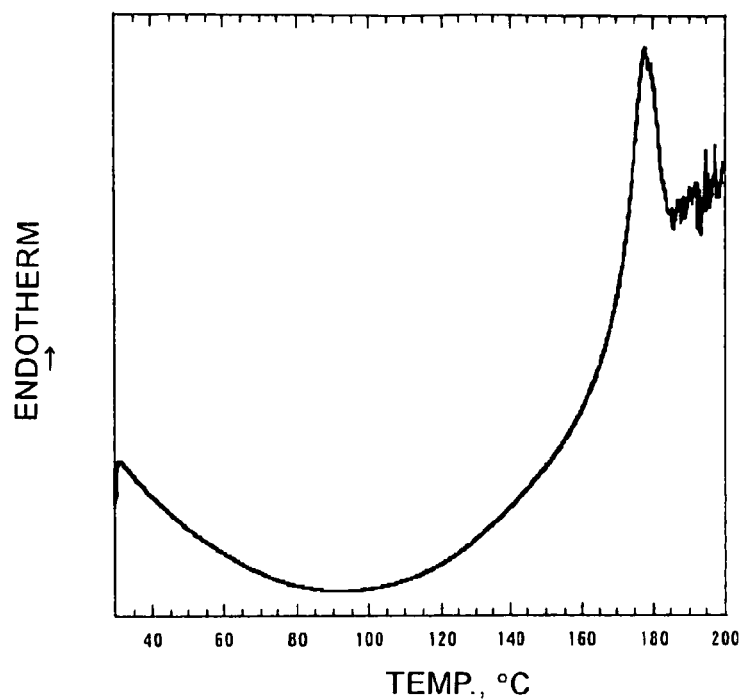
FIG. 13 is a differential scanning calorimetrically measured chart of form II crystal of sulfate prepared in Example 7.
Figure 14:
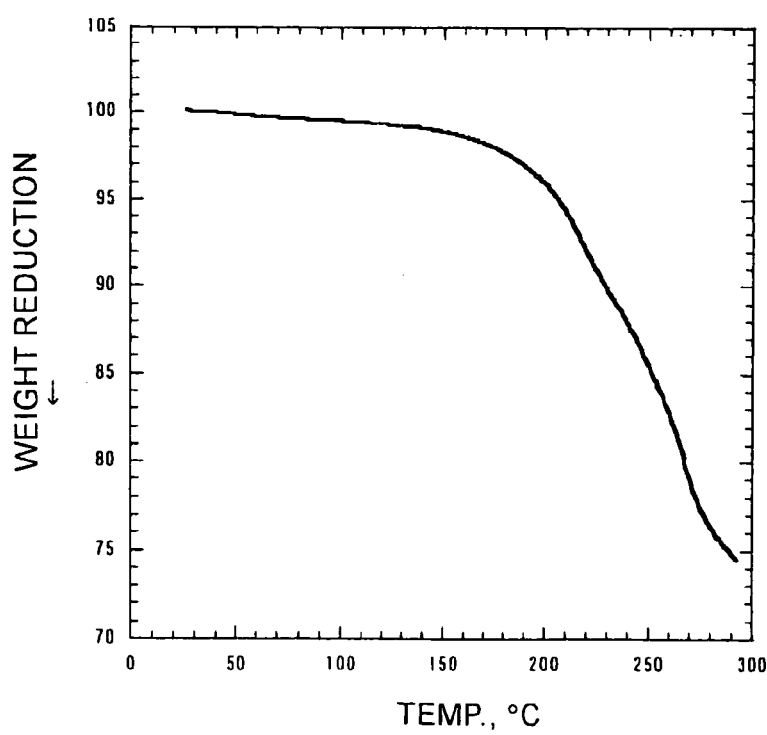
FIG. 14 is a thermogravimetrically measured chart of form II crystal of sulfate prepared in Example 7.

Form II crystal of N-{2-chloro-4-[(6,7-dimethoxy-4-quinolyl)oxy]phenyl}-N'-(5-methyl-3-isoxazolyl)urea sulfate may be produced by the method described in Example 7. The form II crystal of sulfate thus obtained exhibits a powder X-ray diffraction pattern as shown in Table 7 in Example 7. Further, form II crystal of the sulfate exhibits a differential scanning calorimetrically measured chart as shown in FIG. 13 in which an endothermic peak exists at a temperature around 180° C. Furthermore, form II crystal of the sulfate exhibits a thermogravimetrically measured chart as shown in FIG. 14. Form II crystal of the sulfate according to the present invention typically has the above features.

Crystal of Methanesulfonate

The methanesulfonate of N-{2-chloro-4-[(6,7-dimethoxy-4-quinolyl)oxy]phenyl}-N'-(5-methyl-3-isoxazolyl)urea may take crystalline form I, II, III, IV, or V.

Form I Crystal of Methanesulfonate

Form I crystal of N-{2-chloro-4-[(6,7-dimethoxy-4-quinolyl)oxy]phenyl}-N'-(5-methyl-3-isoxazolyl)urea methanesulfonate is monomethanesulfonate.

Figure 15:
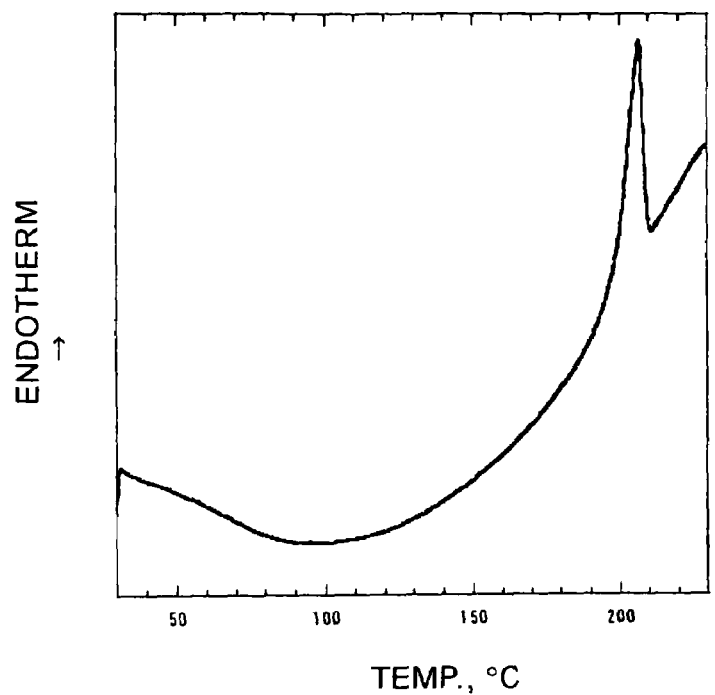
FIG. 15 is a differential scanning calorimetrically measured chart of form I crystal of methanesulfonate prepared in Example 8.
Figure 16:
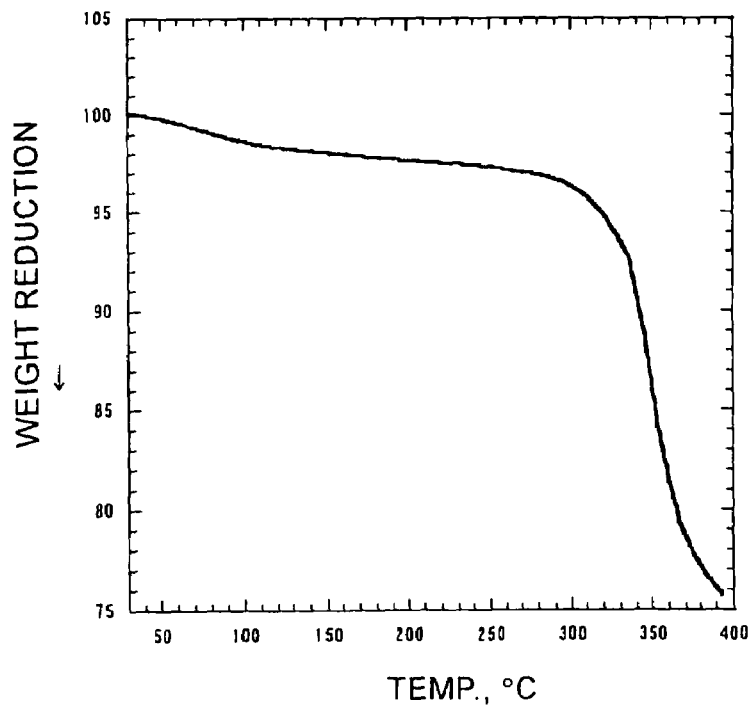
FIG. 16 is a thermogravimetrically measured chart of form I crystal of methanesulfonate prepared in Example 8.

Form I crystal of N-{2-chloro-4-[(6,7-dimethoxy-4-quinolyl)oxy]phenyl}-N'-(5-methyl-3-isoxazolyl)urea methanesulfonate may be produced by the method described in Example 8. The form I crystal of methanesulfonate thus obtained exhibits a powder X-ray diffraction pattern as shown in Table 8 in Example 8. Further, form I crystal of the methanesulfonate exhibits a differential scanning calorimetrically measured chart as shown in FIG. 15 in which an endothermic peak exists at a temperature around 210° C. Furthermore, form I crystal of the methanesulfonate exhibits a thermogravimetrically measured chart as shown in FIG. 16. Form I crystal of the methanesulfonate according to the present invention typically has the above features.

Form II Crystal of Methanesulfonate

Figure 17:
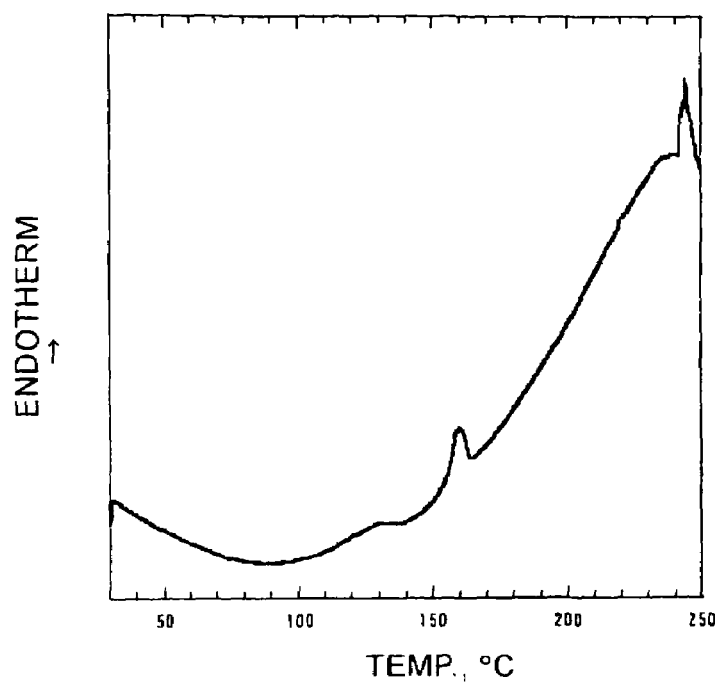
FIG. 17 is a differential scanning calorimetrically measured chart of form II crystal of methanesulfonate prepared in Example 9.
Figure 18:
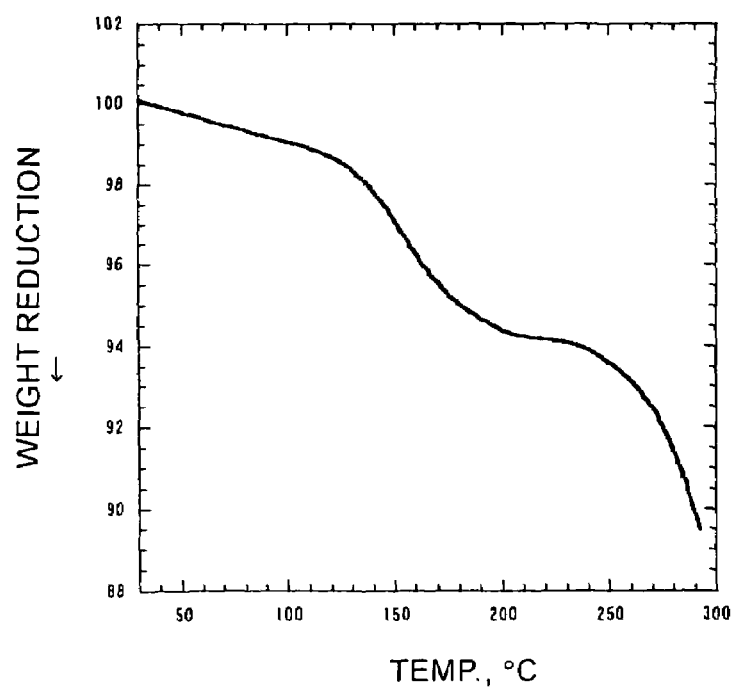
FIG. 18 is a thermogravimetrically measured chart of form II crystal of methanesulfonate prepared in Example 9.

Form II crystal of N-{2-chloro-4-[(6,7-dimethoxy-4-quinolyl)oxy]phenyl}-N'-(5-methyl-3-isoxazolyl)urea methanesulfonate may be produced by the method described in Example 9. The form II crystal of methanesulfonate thus obtained exhibits a powder X-ray diffraction pattern as shown in Table 9 in Example 9. Further, form II crystal of the methanesulfonate exhibits a differential scanning calorimetrically measured chart as shown in FIG. 17 in which endothermic peaks exist at temperatures around 160° C. and 240° C. Furthermore, form II crystal of the methanesulfonate exhibits a thermogravimetrically measured chart as shown in FIG. 18. Form II crystal of the methanesulfonate according to the present invention typically has the above features.

Form III Crystal of Methanesulfonate

Figure 19:
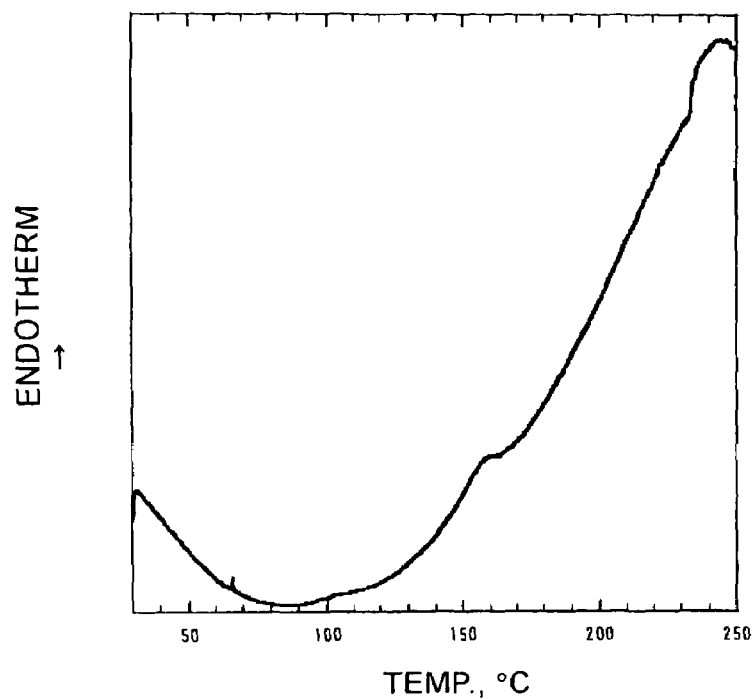
FIG. 19 is a differential scanning calorimetrically measured chart of form III crystal of methanesulfonate prepared in Example 10.
Figure 20:
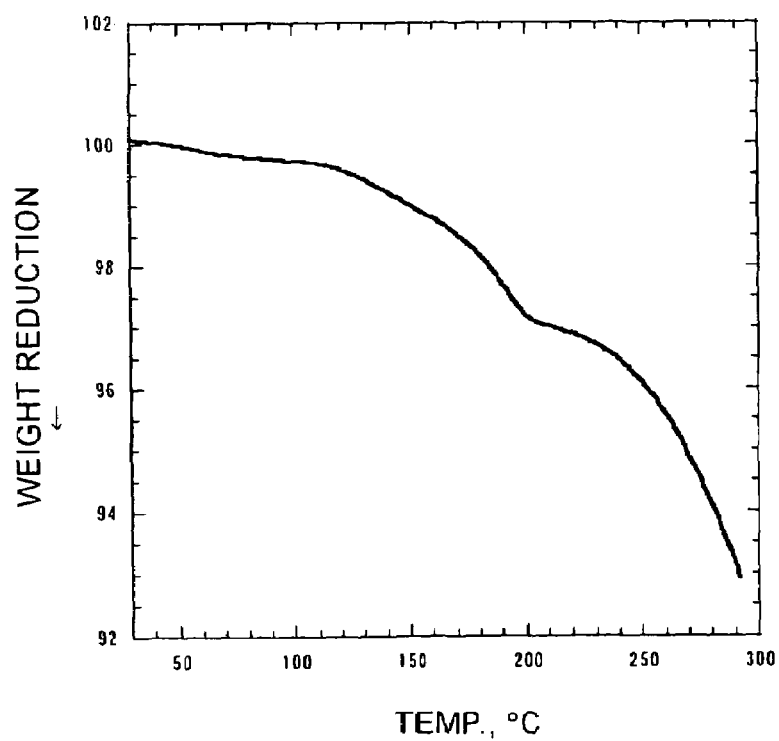
FIG. 20 is a thermogravimetrically measured chart of form III crystal of methanesulfonate prepared in Example 10.

Form III crystal of N-{2-chloro-4-[(6,7-dimethoxy-4-quinolyl)oxy]phenyl}-N'-(5-methyl-3-isoxazolyl)urea methanesulfonate may be produced by the method described in Example 10. The form III crystal of methanesulfonate thus obtained exhibits a powder X-ray diffraction pattern as shown in Table 10 in Example 10. Further, form III crystal of the methanesulfonate exhibits a differential scanning calorimetrically measured chart as shown in FIG. 19 in which endothermic peaks exist at temperatures around 160° C. and 240° C. Furthermore, form III crystal of the methanesulfonate exhibits a thermogravimetrically measured chart as shown in FIG. 20. Form III crystal of the methanesulfonate according to the present invention typically has the above features.

Form IV Crystal of Methanesulfonate

Figure 21:
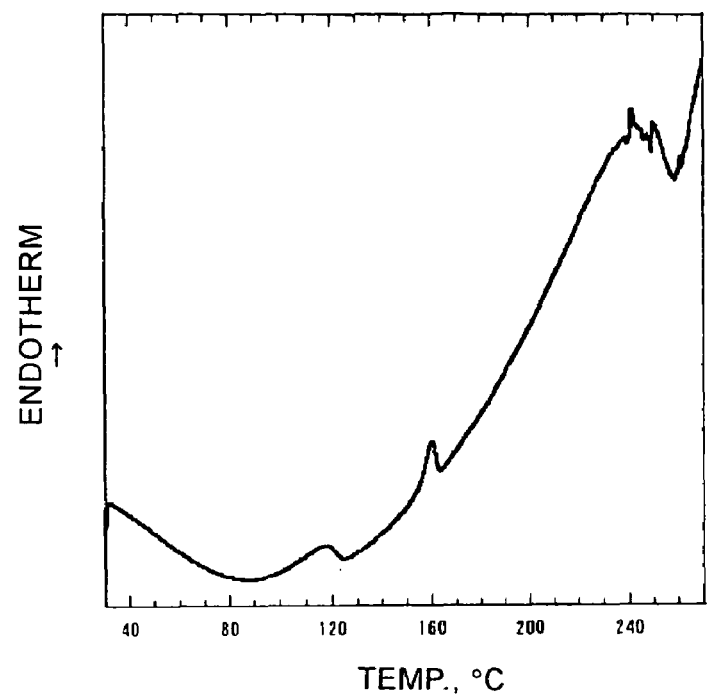
FIG. 21 is a differential scanning calorimetrically measured chart of form IV crystal of methanesulfonate prepared in Example 11.
Figure 22:
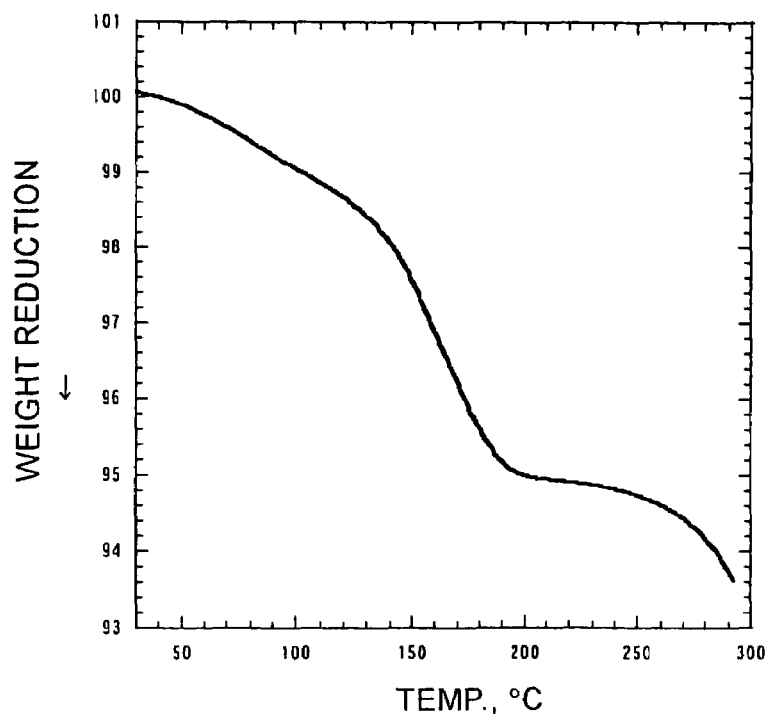
FIG. 22 is a thermogravimetrically measured chart of form IV crystal of methanesulfonate prepared in Example 11.

Form IV crystal of N-{2-chloro-4-[(6,7-dimethoxy-4-quinolyl)oxy]phenyl}-N'-(5-methyl-3-isoxazolyl)urea methanesulfonate may be produced by the method described in Example 11. The form IV crystal of methanesulfonate thus obtained exhibits a powder X-ray diffraction pattern as shown in Table 11 in Example 11. Further, form IV crystal of the methanesulfonate exhibits a differential scanning calorimetrically measured chart as shown in FIG. 21 in which endothermic peaks exist at temperatures around 120° C., 160° C., and 240° C. Furthermore, form IV crystal of the methanesulfonate exhibits a thermogravimetrically measured chart as shown in FIG. 22. Form IV crystal of the methanesulfonate according to the present invention typically has the above features.

Form V Crystal of Methanesulfonate

Figure 23:
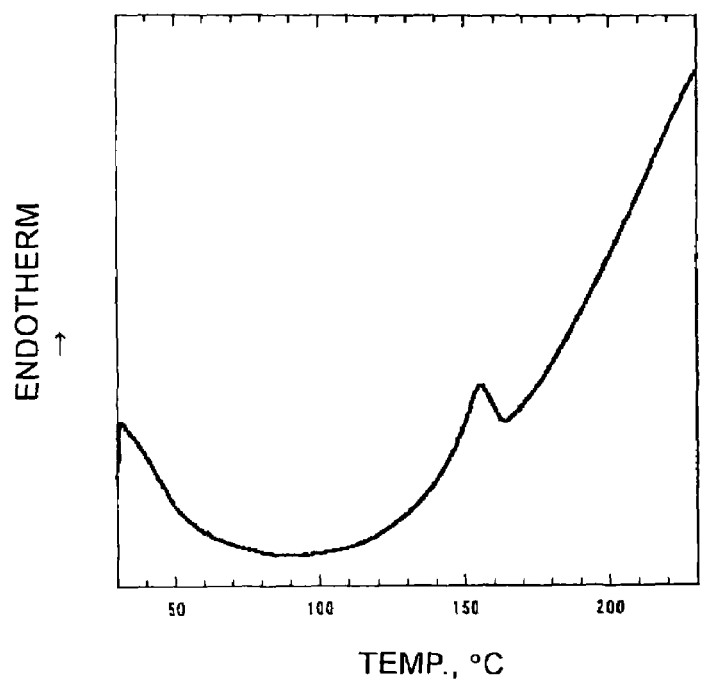
FIG. 23 is a differential scanning calorimetrically measured chart of form V crystal of methanesulfonate prepared in Example 12.
Figure 24:
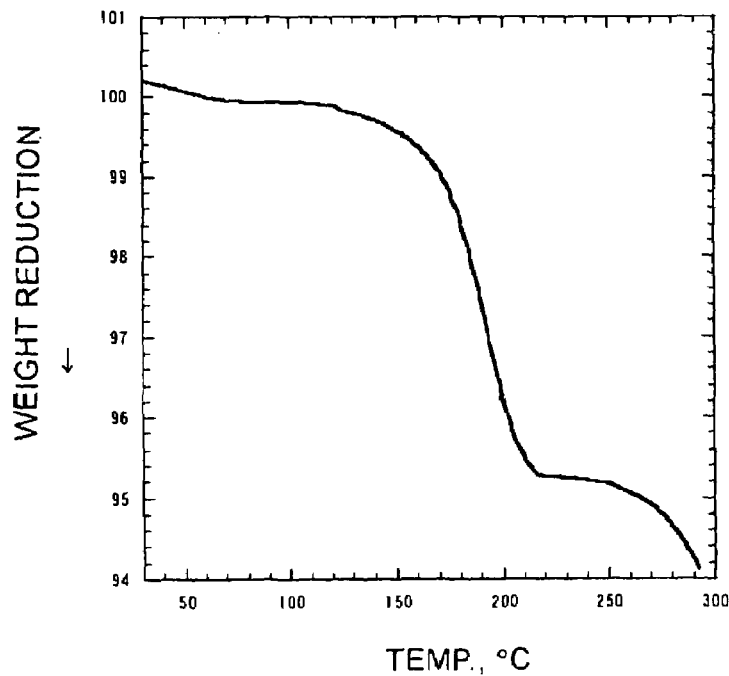
FIG. 24 is a thermogravimetrically measured chart of form V crystal of methanesulfonate prepared in Example 12.

Form V crystal of N-{2-chloro-4-[(6,7-dimethoxy-4-quinolyl)oxy]phenyl}-N'-(5-methyl-3-isoxazolyl)urea methanesulfonate may be produced by the method described in Example 12. The form V crystal of methanesulfonate thus obtained exhibits a powder X-ray diffraction pattern as shown in Table 12 in Example 12. Further, form V crystal of the methanesulfonate exhibits a differential scanning calorimetrically measured chart as shown in FIG. 23 in which an endothermic peak exists at a temperature around 160° C. Furthermore, form V crystal of the methanesulfonate exhibits a thermogravimetrically measured chart as shown in FIG. 24. Form V crystal of the methanesulfonate according to the present invention typically has the above features.

Crystal of p-toluenesulfonate

The p-toluenesulfonate of N-{2-chloro-4-[(6,7-dimethoxy-4-quinolyl)oxy]phenyl}-N'-(5-methyl-3-isoxazolyl)urea may take crystalline form I, II, or III.

Form I Crystal of p-toluenesulfonate

Form I crystal of N-{2-chloro-4-[(6,7-dimethoxy-4-quinolyl)oxy]phenyl}-N'-(5-methyl-3-isoxazolyl)urea p-toluenesulfonate is p-toluenesulfonic acid monoadduct and monohydrate (mono-p-toluenesulfonate monohydrate). For form I crystal of the p-toluenesulfonate, in the differential scanning calorimetry, an endothermic peak was observed at a temperature around 120° C.; in the thermogravimetry, a 3.3% weight reduction was observed between 100° C. and 160° C.; and, in the water content measurement, the water content was found to be 2.8%. Based on these results, the crystal was determined to be monohydrate.

Accordingly, in one preferred embodiment of the present invention, the crystal of the p-toluenesulfonate according to the present invention is a crystal of p-toluenesulfonic acid monoadduct and monohydrate. More preferably, this crystal is form I crystal of p-toluenesulfonate.

Form I crystal of N-{2-chloro-4-[(6,7-dimethoxy-4-quinolyl)oxy]phenyl}-N'-(5-methyl-3-isoxazolyl)urea p-toluenesulfonate may be produced by the method described in Example 13. The form I crystal of the p-toluenesulfonate thus obtained has a powder X-ray diffraction pattern as shown in Table 13 in Example 13.

Accordingly, in one preferred embodiment of the present invention, the crystal of the salt according to the present invention is such that the salt is p-toluenesulfonic acid monoadduct and monohydrate and, in powder X-ray diffractometry, the salt has peaks with not less than 30% relative intensity at diffraction angles (2θ) shown in Table A-3 below. More preferably, the relative intensity at the above diffraction angles (2θ) is not less than 40%, more preferably not less than 50%.

TABLE A-3

| Diffraction angle (2θ) |
| --- |
| 4.92 ± X |
| 9.48 ± X |
| 16.17 ± X |
| 16.85 ± X |
| 19.03 ± X |
| 24.36 ± X |
| 25.27 ± X |
| 26.88 ± X | wherein X is 0 to 0.20, preferably 0 to 0.15, more preferably 0 to 0.10, still more preferably 0 to 0.05.

In a more preferred embodiment of the present invention, the crystal of the salt according to the present invention is such that the salt is p-toluenesulfonic acid monoadduct and monohydrate and, in powder X-ray diffractometry, the salt has peaks with not less than 10% relative intensity at diffraction angles (2θ) shown in Table B-3 below. More preferably, the relative intensity at the above diffraction angles (2θ) is not less than 15%, more preferably not less than 20%.

TABLE B-3

| Diffraction angle (2θ) |
| --- |
| 4.92 ± X |
| 9.48 ± X |
| 15.74 ± X |
| 16.17 ± X |
| 16.85 ± X |
| 17.19 ± X |
| 17.55 ± X |
| 19.03 ± X |
| 21.19 ± X |
| 21.36 ± X |
| 21.80 ± X |
| 22.30 ± X |
| 23.75 ± X |
| 23.93 ± X |
| 24.36 ± X |
| 25.27 ± X |
| 25.78 ± X |
| 26.88 ± X |
| 28.15 ± X |
| 28.41 ± X | wherein X is 0 to 0.20, preferably 0 to 0.15, more preferably 0 to 0.10, still more preferably 0 to 0.05.

Figure 25:
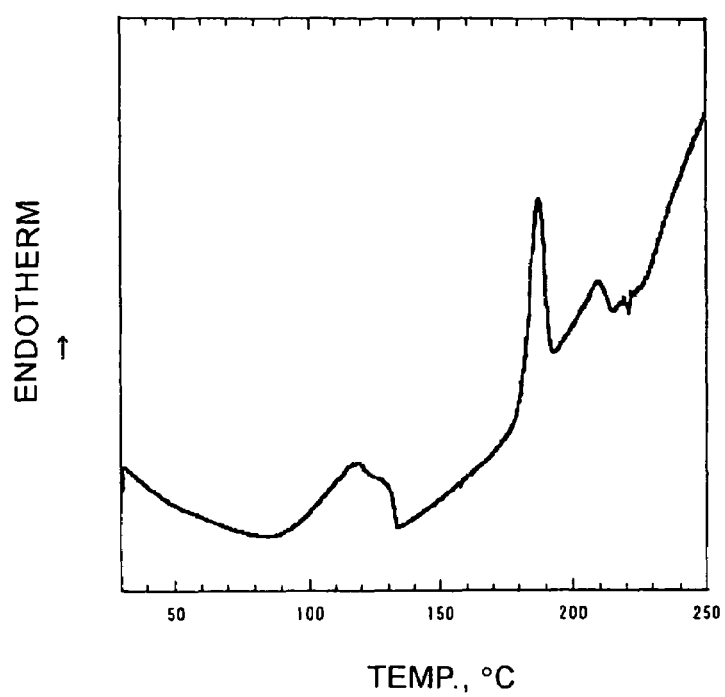
FIG. 25 is a differential scanning calorimetrically measured chart of form I crystal of p-toluenesulfonate prepared in Example 13.
Figure 26:
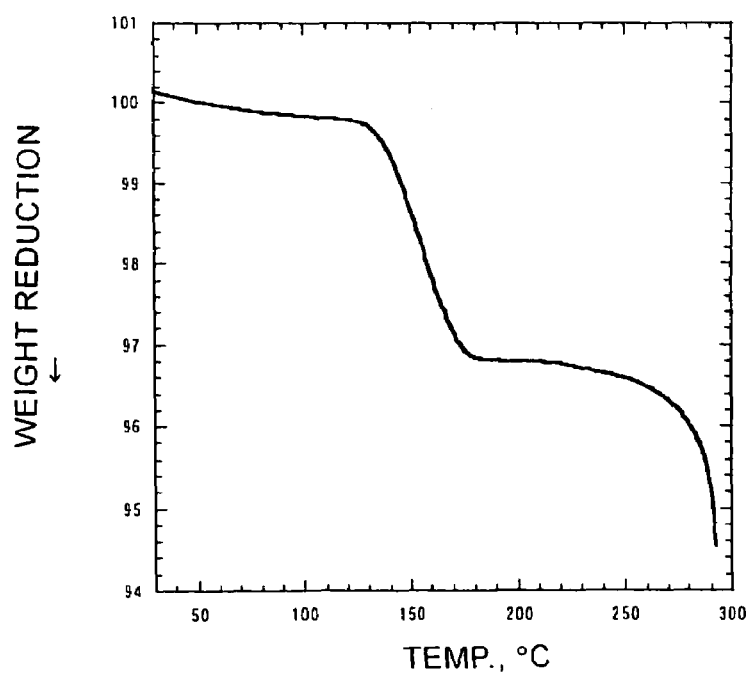
FIG. 26 is a thermogravimetrically measured chart of form I crystal of p-toluenesulfonate prepared in Example 13.

Further, form I crystal of the p-toluenesulfonate exhibits a differential scanning calorimetrically measured chart as shown in FIG. 25 in which endothermic peaks exist at temperatures around 120° C. and 180° C. Furthermore, form I crystal of the p-toluenesulfonate exhibits a thermogravimetrically measured chart as shown in FIG. 26. Form I crystal of the p-toluenesulfonate according to the present invention typically has the above features.

Form II Crystal of p-toluenesulfonate

Form II crystal of N-{2-chloro-4-[(6,7-dimethoxy-4-quinolyl)oxy]phenyl}-N'-(5-methyl-3-isoxazolyl)urea p-toluenesulfonate is p-toluenesulfonic acid monoadduct and monohydrate (mono-p-toluenesulfonate monohydrate). For form II crystal of the p-toluenesulfonate, in the differential scanning calorimetry, an endothermic peak was observed at a temperature around 120° C.; in the thermogravimetry, a 3.4% weight reduction was observed between 100° C. and 160° C.; and, in the water content measurement, the water content was found to be 3.1%. Based on these results, the crystal was determined to be monohydrate.

Accordingly, in one preferred embodiment of the present invention, the crystal of the p-toluenesulfonate according to the present invention is a crystal of p-toluenesulfonic acid monoadduct and monohydrate. More preferably, this crystal is form II crystal of p-toluenesulfonate.

Form II crystal of N-{2-chloro-4-[(6,7-dimethoxy-4-quinolyl)oxy]phenyl}-N'-(5-methyl-3-isoxazolyl)urea p-toluenesulfonate may be produced by the method described in Example 14. The form II crystal of the p-toluenesulfonate thus obtained has a powder X-ray diffraction pattern as shown in Table 14 in Example 14.

Accordingly, in one preferred embodiment of the present invention, the crystal of the salt according to the present invention is such that the salt is p-toluenesulfonic acid monoadduct and monohydrate and, in powder X-ray diffractometry, the salt has peaks with not less than 30% relative intensity at diffraction angles (2θ) shown in Table A-4 below. More preferably, the relative intensity at the above diffraction angles (2θ) is not less than 40%, more preferably not less than 50%.

TABLE A-4

| Diffraction angle (2θ) |
| --- |
| 4.86 ± X |
| 9.42 ± X |
| 18.93 ± X |
| 21.17 ± X |
| 24.03 ± X |
| 25.57 ± X |
| 27.16 ± X |
| 28.48 ± X | wherein X is 0 to 0.20, preferably 0 to 0.15, more preferably 0 to 0.10, still more preferably 0 to 0.05.

In a more preferred embodiment of the present invention, the crystal of the salt according to the present invention is such that the salt is p-toluenesulfonic acid monoadduct and monohydrate and, in powder X-ray diffractometry, the salt has peaks with not less than 10% relative intensity at diffraction angles (2θ) shown in Table B-4 below. More preferably, the relative intensity at the above diffraction angles (2θ) is not less than 15%, more preferably not less than 20%.

TABLE B-4

| Diffraction angle (2θ) |
| --- |
| 4.86 ± X |
| 9.42 ± X |
| 12.45 ± X |

TABLE B-4-continued

| Diffraction angle (2θ) |
| --- |
| 15.83 ± X |
| 16.16 ± X |
| 16.74 ± X |
| 17.31 ± X |
| 17.62 ± X |
| 18.93 ± X |
| 21.17 ± X |
| 21.82 ± X |
| 22.39 ± X |
| 24.03 ± X |
| 24.31 ± X |
| 25.57 ± X |
| 26.01 ± X |
| 27.16 ± X |
| 28.48 ± X | wherein X is 0 to 0.20, preferably 0 to 0.15, more preferably 0 to 0.10, still more preferably 0 to 0.05.

Further, form II crystal of the p-toluenesulfonate exhibits a differential scanning calorimetrically measured chart as shown in FIG. 27 in which endothermic peaks exist at temperatures around 120° C. and 180° C. Furthermore, form II crystal of the p-toluenesulfonate exhibits a thermogravimetrically measured chart as shown in FIG. 28. Form II crystal of the p-toluenesulfonate according to the present invention typically has the above features.

Form III Crystal of p-toluenesulfonate

Figure 29:
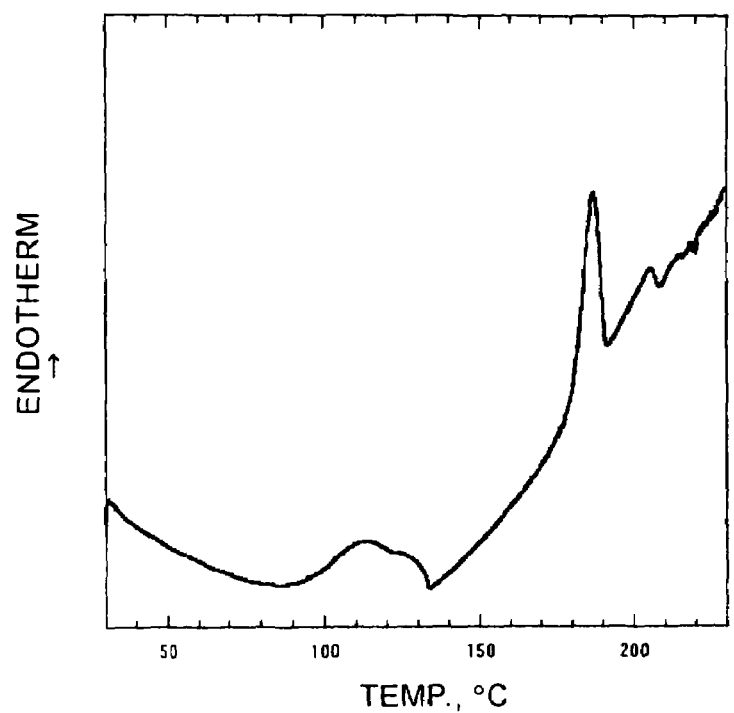
FIG. 29 is a differential scanning calorimetrically measured chart of form III crystal of p-toluenesulfonate prepared in Example 15.
Figure 30:
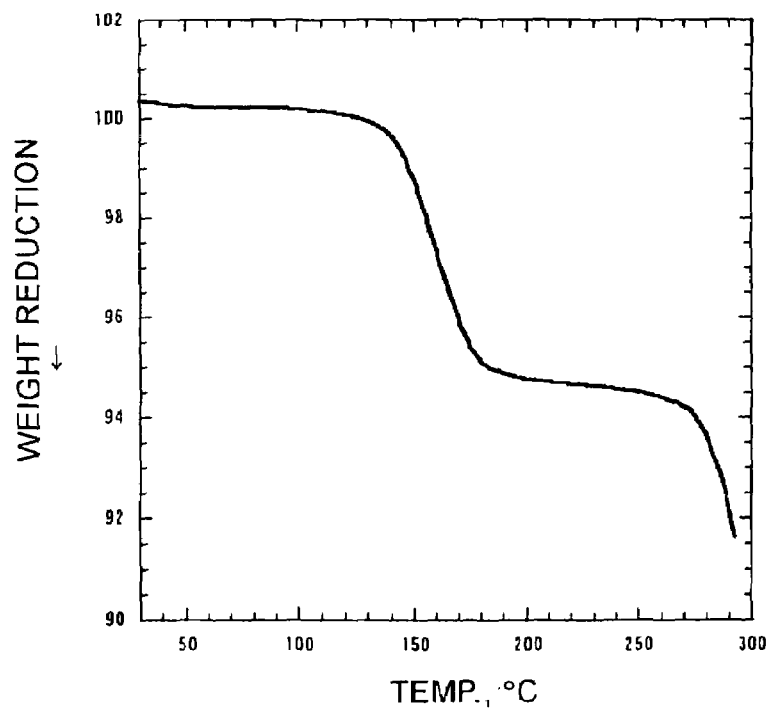
FIG. 30 is a thermogravimetrically measured chart of form III crystal of p-toluenesulfonate prepared in Example 15.

Form III crystal of N-{2-chloro-4-[(6,7-dimethoxy-4-quinolyl)oxy]phenyl}-N'-(5-methyl-3-isoxazolyl)urea p-toluenesulfonate may be produced by the method described in Example 15. The form III crystal of p-toluenesulfonate thus obtained exhibits a powder X-ray diffraction pattern as shown in Table 15 in Example 15. Further, form III crystal of the p-toluenesulfonate exhibits a differential scanning calorimetrically measured chart as shown in FIG. 29 in which endothermic peaks exist at temperatures around 120° C. and 190° C. Furthermore, form III crystal of the p-toluenesulfonate exhibits a thermogravimetrically measured chart as shown in FIG. 30. Form III crystal of the p-toluenesulfonate according to the present invention typically has the above features.

Crystal of Maleate

The maleate of N-{2-chloro-4-[(6,7-dimethoxy-4-quinolyl)oxy]phenyl}-N'-(5-methyl-3-isoxazolyl)urea may take crystalline form I, II, III, or IV.

Form I crystal of N-{2-chloro-4-[(6,7-dimethoxy-4-quinolyl)oxy]phenyl}-N'-(5-methyl-3-isoxazolyl)urea maleate is monomaleate.

Form I Crystal of Maleate

Figure 31:
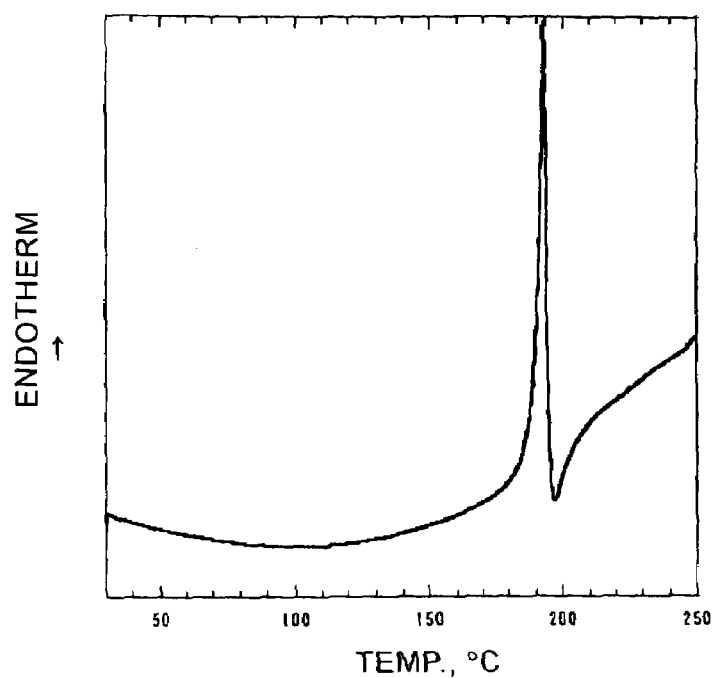
FIG. 31 is a differential scanning calorimetrically measured chart of form I crystal of maleate prepared in Example 16.
Figure 32:
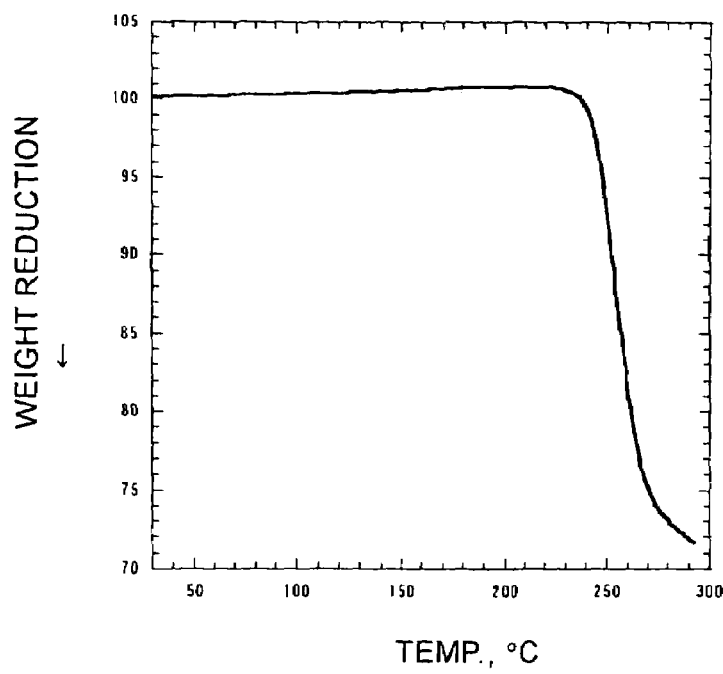
FIG. 32 is a thermogravimetrically measured chart of form I crystal of maleate prepared in Example 16.

Form I crystal of N-{2-chloro-4-[(6,7-dimethoxy-4-quinolyl)oxy]phenyl}-N'-(5-methyl-3-isoxazolyl)urea maleate may be produced by the method described in Example 16. The form I crystal of maleate thus obtained exhibits a powder X-ray diffraction pattern as shown in Table 16 in Example 16. Further, form I crystal of the maleate exhibits a differential scanning calorimetrically measured chart as shown in FIG. 31 in which an endothermic peak exists at a temperature around 190° C. Furthermore, form I crystal of the maleate exhibits a thermogravimetrically measured chart as shown in FIG. 32. Form I crystal of the maleate according to the present invention typically has the above features.

Form II Crystal of Maleate

Form II crystal of N-{2-chloro-4-[(6,7-dimethoxy-4-quinolyl)oxy]phenyl}-N'-(5-methyl-3-isoxazolyl)urea maleate is monomaleate.

Form II crystal of N-{2-chloro-4-[(6,7-dimethoxy-4-quinolyl)oxy]phenyl}-N'-(5-methyl-3-isoxazolyl)urea maleate may be produced by the method described in Example 17. The form II crystal of maleate thus obtained exhibits a powder X-ray diffraction pattern as shown in Table 17 in Example 17.

In one preferred embodiment of the present invention, the crystal of the salt according to the present invention is such that the salt is maleic acid monoadduct and, in powder X-ray diffractometry, the salt has peaks with not less than 10% relative intensity at diffraction angles (2θ) shown in Table B-5 below. More preferably, the relative intensity at the above diffraction angles (2θ) is not less than 15%, more preferably not less than 20%.

TABLE B-5

| Diffraction angle (2θ) |
| --- |
| 4.33 ± X |
| 8.70 ± X |
| 12.19 ± X |
| 12.70 ± X |
| 14.72 ± X |
| 15.88 ± X |
| 17.36 ± X |
| 22.70 ± X |
| 23.06 ± X |
| 23.22 ± X |
| 23.55 ± X |
| 24.06 ± X |
| 24.63 ± X |
| 25.65 ± X |
| 26.06 ± X |
| 27.20 ± X | wherein X is 0 to 0.20, preferably 0 to 0.15, more preferably 0 to 0.10, still more preferably 0 to 0.05.

Figure 33:
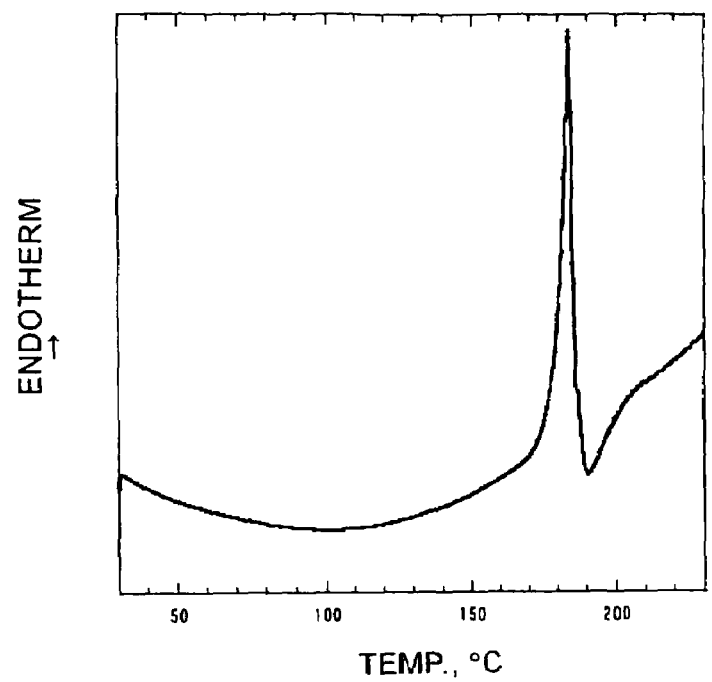
FIG. 33 is a differential scanning calorimetrically measured chart of form II crystal of maleate prepared in Example 17.
Figure 34:
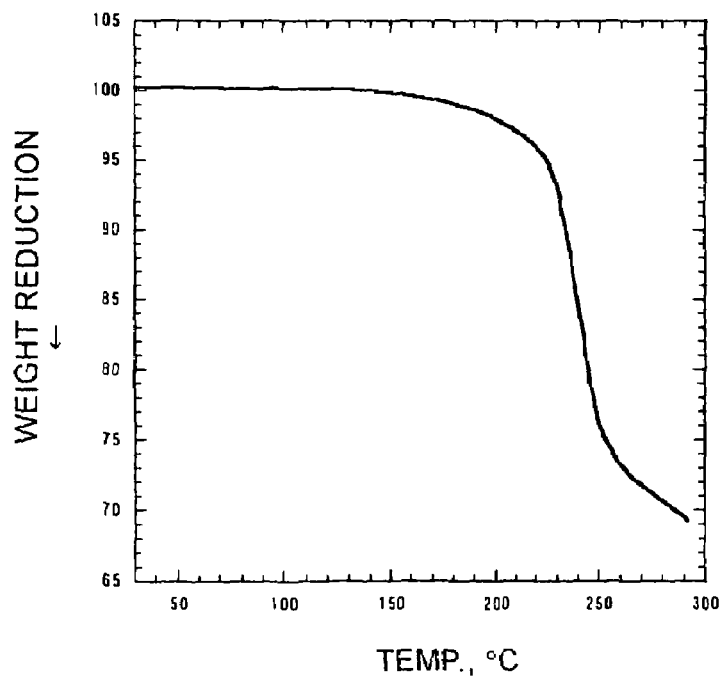
FIG. 34 is a thermogravimetrically measured chart of form II crystal of maleate prepared in Example 17.

Further, form II crystal of the maleate exhibits a differential scanning calorimetrically measured chart as shown in FIG. 33 in which an endothermic peak exists at a temperature around 180° C. Furthermore, form II crystal of the maleate exhibits a thermogravimetrically measured chart as shown in FIG. 34. Form II crystal of the maleate according to the present invention typically has the above features.

Form III Crystal of Maleate

Figure 35:
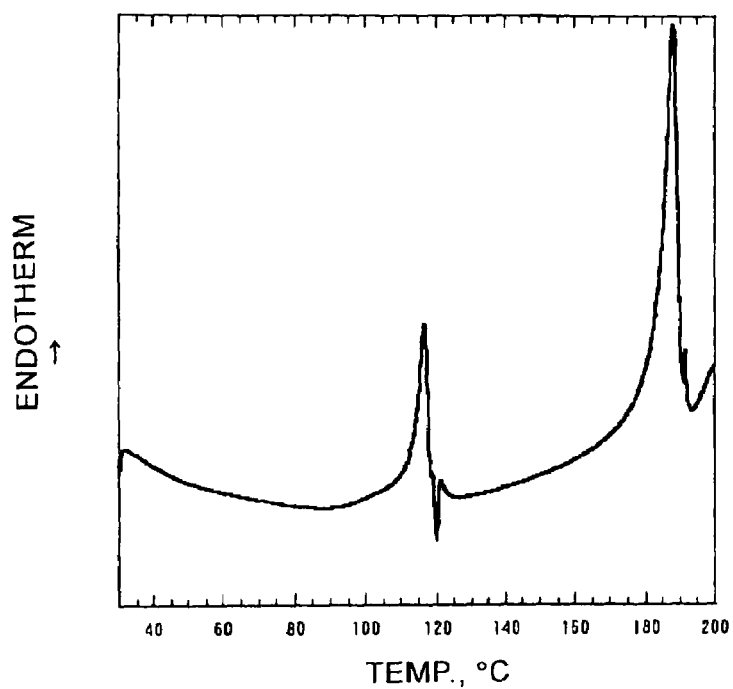
FIG. 35 is a differential scanning calorimetrically measured chart of form III crystal of maleate prepared in Example 18.
Figure 36:
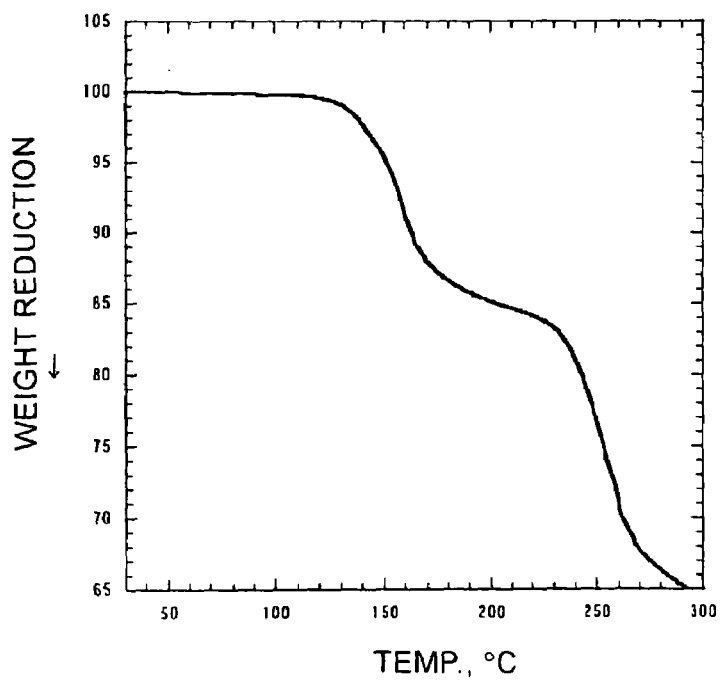
FIG. 36 is a thermogravimetrically measured chart of form III crystal of maleate prepared in Example 18.

Form III crystal of N-{2-chloro-4-[(6,7-dimethoxy-4-quinolyl)oxy]phenyl}-N'-(5-methyl-3-isoxazolyl)urea maleate may be produced by the method described in Example 18. The form III crystal of maleate thus obtained exhibits a powder X-ray diffraction pattern as shown in Table 18 in Example 18. Further, form III crystal of the maleate exhibits a differential scanning calorimetrically measured chart as shown in FIG. 35 in which endothermic peaks exist at temperatures around 110° C. and 190° C. Furthermore, form III crystal of the maleate exhibits a thermogravimetrically measured chart as shown in FIG. 36. Form III crystal of the maleate according to the present invention typically has the above features.

Form IV Crystal of Maleate

Figure 37:
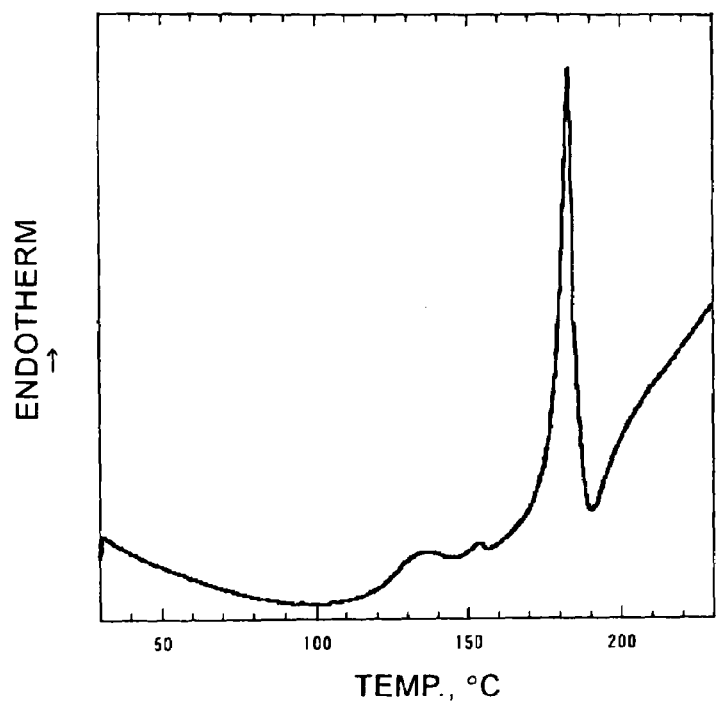
FIG. 37 is a differential scanning calorimetrically measured chart of form IV crystal of maleate prepared in Example 19.
Figure 38:
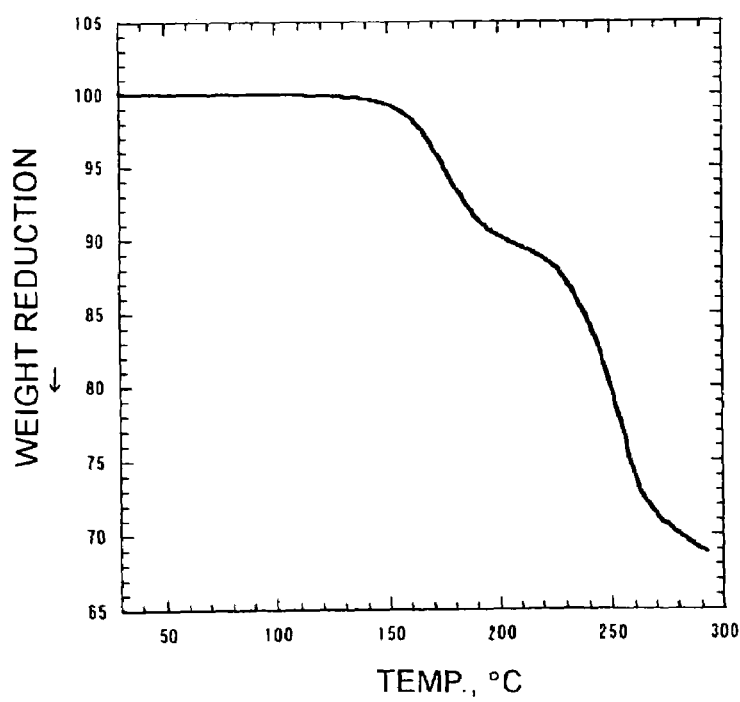
FIG. 38 is a thermogravimetrically measured chart of form IV crystal of maleate prepared in Example 19.

Form IV crystal of N-{2-chloro-4-[(6,7-dimethoxy-4-quinolyl)oxy]phenyl}-N'-(5-methyl-3-isoxazolyl)urea maleate may be produced by the method described in Example 19. The form IV crystal of maleate thus obtained exhibits a powder X-ray diffraction pattern as shown in Table 19 in Example 19. Further, form IV crystal of the maleate exhibits a differential scanning calorimetrically measured chart as shown in FIG. 37 in which endothermic peaks exist at temperatures around 130° C. and 180° C. Furthermore, form IV crystal of the maleate exhibits a thermogravimetrically measured chart as shown in FIG. 38. Form IV crystal of the maleate according to the present invention typically has the above features.

The results of Test Example 1 which will be described later show that form I crystal and form II crystal of hydrochloride, form I crystal of nitrate, form I crystal of sulfate, form I crystal of methanesulfonate, form I crystal and form II crystal of p-toluenesulfonate, and form I crystal and form II crystal of maleate have excellent stability under high temperature (73° C.) conditions.

The results of Test Example 2 show that form I crystal and form II crystal of hydrochloride, form I crystal of nitrate, form I crystal of methanesulfonate, form I crystal and form II crystal of p-toluenesulfonate, form I crystal and form II crystal of maleate have excellent stability under high humidity (40° C., 75% RH) conditions.

The results of Test Example 3 show that form I crystal and form II crystal of hydrochloride, form I crystal of nitrate, form I crystal of methanesulfonate, form I crystal and form II crystal of p-toluenesulfonate, and form II crystal of maleate have excellent stability against physical stress.

The results of Test Example 4 show that form I crystal and form II crystal of hydrochloride, form I crystal and form II crystal of p-toluenesulfonate, form I crystal and form II crystal of maleate have a low level of hygroscopicity.

In formulating pharmaceutical compounds, it is desired that specific crystalline forms which can offer a given effect while maintaining pharmacological properties as pharmaceutical compounds, that is, crystalline forms stable against thermal stress and physical stress, are formulated. Further, pharmaceutical compounds which are stable under high humidity conditions and have a low level of hygroscopicity are desired. In particular, in the case of formulation into pharmaceutical preparations for oral administration, since a physical change such as a change in crystalline form directly affects absorption of the preparations, desirably, the crystals have a high level of physical stability.

Thus, in a preferred embodiment of the present invention, the crystals of salts according to the present invention are form I crystal and form II crystal of hydrochloride, form I crystal of nitrate, form I crystal of sulfate, form I crystal of methanesulfonate, form I crystal and form II crystal of p-toluenesulfonate, and form I crystal and form II crystal of maleate. More preferably, the crystals of salts according to the present invention are form I crystal and form II crystal of hydrochloride, form I crystal of nitrate, form I crystal of methanesulfonate, form I crystal and form II crystal of p-toluenesulfonate, and form I crystal and form II crystal of maleate.

In a more preferred embodiment of the present invention, the crystals of salts according to the present invention are form I crystal and form II crystal of hydrochloride, form I crystal and form II crystal of p-toluenesulfonate, and form II crystal of maleate.

In a still more preferred embodiment of the present invention, the crystals of salts according to the present invention are form I crystal and form II crystal of hydrochloride, and form I crystal and form II crystal of p-toluenesulfonate. For these crystals, industrial production which can realize stable supply can be relatively easily established.

In a particularly preferred embodiment of the present invention, the crystal of a salt according to the present invention is a crystal of N-{2-chloro-4-[(6,7-dimethoxy-4- quinolyl)oxy]phenyl}-N'-(5-methyl-3-isoxazolyl)urea hydrochloride. In the crystal of this hydrochloride, the salt is hydrochloride monoadduct. The hydrochloride is preferably solvent adduct. In this case, the solvent is preferably water. The hydrochloride is more preferably water monoadduct. Therefore, the hydrochloride is more preferably hydrochloric acid monoadduct and monohydrate.

In the most preferred embodiment of the present invention, the crystal of a salt according to the present invention is form I crystal of N-{2-chloro-4-[(6,7-dimethoxy-4-quinolyl)oxy]phenyl}-N'-(5-methyl-3-isoxazolyl)urea hydrochloride. This form I crystal of hydrochloride has all physicochemical properties that are desired as pharmaceutical preparations for oral administration. The powder X-ray diffraction pattern of form I crystal of hydrochloride is not similar to that of other crystalline forms of hydrochloride (for example, form II crystal and form III crystal). Therefore, the mixing ratio of crystalline forms can be easily determined. Further, in suspending form I crystal of hydrochloride in an aqueous methylcellulose solution used in an administration solution for rodents, this crystal does not undergo a deterioration that results in the formation of gel which cannot be administered without difficulties. Therefore, problems with administration are less likely to occur. Also in this respect, form I crystal of hydrochloride is advantageous.

Production of Crystal of Salt According to the Invention

Production of Crystal of Hydrochloride

According to the present invention, there is provided a process for producing a crystal of a hydrochloride of N-{2-chloro-4-[(6,7-dimethoxy-4-quinolyl)oxy]phenyl}-N'-(5-methyl-3-isoxazolyl)urea, said process comprising the steps of: adding hydrochloric acid and an alcoholic solvent and/or water to a solution of N-{2-chloro-4-[(6,7-dimethoxy-4-quinolyl)oxy]phenyl}-N'-(5-methyl-3-isoxazolyl)urea in an aprotic polar solvent; and precipitating crystals from the solution.

In a preferred embodiment of the present invention, form I or form II crystal of a hydrochloride of N-{2-chloro-4-[(6,7-dimethoxy-4-quinolyl)oxy]phenyl}-N'-(5-methyl-3-isoxazolyl)urea can be produced by dissolving N-{2-chloro-4-[(6,7-dimethoxy-4-quinolyl)oxy]phenyl}-N'-(5-methyl-3-isoxazolyl)urea in an aprotic polar solvent in a temperature range of about 50° C. to boiling point to prepare a solution, then cooling the solution preferably to room temperature, adding hydrochloric acid and an alcoholic solvent and/or water, and precipitating crystals from the solution.

The concentration of hydrochloric acid is preferably 10 N to 14 N, more preferably about 12 N.

The aprotic polar solvent is preferably N,N-dimethylformamide or N,N-dimethylacetamide, more preferably N,N-dimethylformamide.

The alcoholic solvent and/or water are preferably ethanol and water or 1-propanol.

In one preferred embodiment of the present invention, there is provided a process for producing form I crystal of a hydrochloride of N-{2-chloro-4-[(6,7-dimethoxy-4-quinolyl)oxy]phenyl}-N'-(5-methyl-3-isoxazolyl)urea, said process comprising the steps of: adding hydrochloric acid and ethanol to a solution of N-{2-chloro-4-[(6,7-dimethoxy-4-quinolyl)oxy]phenyl}-N'-(5-methyl-3-isoxazolyl)urea in an aprotic polar solvent; and precipitating crystals from the solution. In this case, more preferably, in addition to hydrochloric acid and ethanol, water is added.

In another preferred embodiment of the present invention, there is provided a process for producing form II crystal of a hydrochloride of N-{2-chloro-4-[(6,7-dimethoxy-4-quinolyl)oxy]phenyl}-N'-(5-methyl-3-isoxazolyl)urea, said process comprising the steps of: adding hydrochloric acid and 1-propanol to a solution of N-{2-chloro-4-[(6,7-dimethoxy-4-quinolyl)oxy]phenyl}-N'-(5-methyl-3-isoxazolyl)urea in an aprotic polar solvent; and precipitating crystals from the solution.

The amount of the aprotic organic solvent may be about 5 to about 50 times (V/W), preferably about 7 to 10 times (V/W), that of the amount of N-{2-chloro-4-[(6,7-dimethoxy-4-quinolyl)oxy]phenyl}-N'-(5-methyl-3-isoxazolyl)urea.

In another embodiment of the present invention, a crystal, particularly form III crystal, of N-{2-chloro-4-[(6,7-dimethoxy-4-quinolyl)oxy]phenyl}-N'-(5-methyl-3-isoxazolyl)urea hydrochloride may be produced by adding an alcoholic organic solvent, for example, 1-butanol, and hydrochloric acid to N-{2-chloro-4-[(6,7-dimethoxy-4-quinolyl)oxy]phenyl}-N'-(5-methyl-3-isoxazolyl)urea, dissolving them in each other, and then cooling the solution.

Specifically, for example, form I to III crystals of hydrochloride can be produced by any of the methods described in Examples 1 to 3 which will be described later.

Production of Crystal of Nitrate

According to the present invention, form I or form II crystal of nitrate of N-{2-chloro-4-[(6,7-dimethoxy-4-quinolyl)oxy]phenyl}-N'-(5-methyl-3-isoxazolyl)urea can be produced by adding an alcoholic organic solvent, for example, methanol, and nitric acid to N-{2-chloro-4-[(6,7-dimethoxy-4-quinolyl)oxy]phenyl}-N'-(5-methyl-3-isoxazolyl)urea, stirring the mixture, filtering the stirred mixture, dissolving the filtered product in an organic solvent and/or water under heating conditions (for example, at about 100° C.), cooling the solution (for example, to room temperature or about 5° C.), and optionally adding ethyl acetate or the like, to precipitate crystals.

The organic solvent and/or water may be, for example, methanol and water, or N,N-dimethylformamide.

Specifically, for example, form I or form II crystal of nitrate can be produced by the method described in Example 4 or 5 which will be described later.

Production of Crystal of Sulfate

According to the present invention, form I or form II crystal of sulfate of N-{2-chloro-4-[(6,7-dimethoxy-4-quinolyl)oxy]phenyl}-N'-(5-methyl-3-isoxazolyl)urea can be produced by adding an alcoholic organic solvent, for example, methanol, and concentrated sulfuric acid to N-{2-chloro-4-[(6,7-dimethoxy-4-quinolyl)oxy]phenyl}-N'-(5-methyl-3-isoxazolyl)urea, stirring the mixture, filtering the stirred mixture, dissolving the filtered product in an organic solvent and/or water under heating conditions (for example, at about 140° C.), and cooling the solution (for example, to about 5° C.), to precipitate crystals.

The organic solvent and/or water may be, for example, acetonitrile and water, or N,N-dimethylformamide.

Specifically, for example, form I or form II crystal of sulfate can be produced by the method described in Example 6 or 7 which will be described later.

Production of Crystal of Methanesulfonate

According to the present invention, form I to V crystals of methanesulfonate of N-{2-chloro-4-[(6,7-dimethoxy-4-quinolyl)oxy]phenyl}-N'-(5-methyl-3-isoxazolyl)urea can be produced by adding an alcoholic organic solvent, for example, methanol, and methanesulfonic acid to N-{2-chloro-4-[(6,7-dimethoxy-4-quinolyl)oxy]phenyl}-N'-(5-methyl-3-isoxazolyl)urea, stirring the mixture, filtering the stirred mixture, dissolving the filtered product in a predetermined organic solvent under heating conditions (for example, at about 80 to 100° C.), cooling the solution (for example, to room temperature or about 5° C.), and optionally adding other solvent, to precipitate crystals.

For example, methanol, ethanol, N,N-dimethylformamide, N,N-dimethylacetamide, acetonitrile, acetonitrile, and methanol may be mentioned as the predetermined organic solvent. For example, acetonitrile and ethyl acetate may be mentioned as the other solvent.

Specifically, for example, form I to V crystals of methanesulfonate can be produced by any of the methods in Examples 8 to 12, which will be described later.

Production of Crystal of p-Toluenesulfonate

According to the present invention, a crystal (form I to III) of p-toluenesulfonate of N-{2-chloro-4-[(6,7-dimethoxy-4-quinolyl)oxy]phenyl}-N'-(5-methyl-3-isoxazolyl)urea can be produced by dissolving a p-toluenesulfonate of N-{2-chloro-4-[(6,7-dimethoxy-4-quinolyl)oxy]phenyl}-N'-(5-methyl-3-isoxazolyl)urea in an organic solvent and/or water under heating conditions (for example, at about 100° C.) to prepare a solution, cooling the solution (for example, to room temperature), and optionally adding water dropwise followed by cooling (for example, to about 5° C.), to precipitate crystals.

For example, methanol and water, or N,N-dimethylacetamide may be mentioned as the organic solvent and/or water.

The amount of the organic solvent and/or water may be about 5 to about 50 times (V/W), preferably about 10 to 30 times (V/W), that of the amount of N-{2-chloro-4-[(6,7-dimethoxy-4-quinolyl)oxy]phenyl}-N'-(5-methyl-3-isoxazolyl)urea.

The p-toluenesulfonate of N-{2-chloro-4-[(6,7-dimethoxy-4-quinolyl)oxy]phenyl}-N'-(5-methyl-3-isoxazolyl)urea used in the production of the crystal of the salt may be prepared by adding acetonitrile to N-{2-chloro-4-[(6,7-dimethoxy-4-quinolyl)oxy]phenyl}-N'-(5-methyl-3-isoxazolyl)urea, adding a solution of p-toluenesulfonic acid monohydrate in acetonitrile dropwise thereto, and stirring the mixture. Accordingly, the production process of the crystal of p-toluenesulfonate according to the present invention may further include the step of producing the above p-toluenesulfonate.

In one preferred embodiment of the present invention, there is provided a process for producing form I crystal of p-toluenesulfonate of N-{2-chloro-4-[(6,7-dimethoxy-4-quinolyl)oxy]phenyl}-N'-(5-methyl-3-isoxazolyl)urea, said process comprising the steps of: adding p-toluenesulfonic acid to a solvent composed of N-{2-chloro-4-[(6,7-dimethoxy-4-quinolyl)oxy]phenyl}-N'-(5-methyl-3-isoxazolyl)urea dissolved in acetonitrile to prepare a solution, precipitating crystals from the solution, dissolving the crystals in methanol and water, and precipitating crystals from the solution optionally by cooling the solution (for example, to room temperature).

In another preferred embodiment of the present invention, there is provided a process for producing form II crystal of p-toluenesulfonate of N-{2-chloro-4-[(6,7-dimethoxy-4-quinolyl)oxy]phenyl}-N'-(5-methyl-3-isoxazolyl)urea, said process comprising the steps of: adding p-toluenesulfonic acid to a solvent composed of N-{2-chloro-4-[(6,7-dimethoxy-4-quinolyl)oxy]phenyl}-N'-(5-methyl-3-isoxazolyl)urea dissolved in acetonitrile to prepare a solution, precipitating crystals from the solution, dissolving the crystals in N,N-dimethylformamide to prepare a solution, adding water to the solution, and precipitating crystals from the solution optionally by cooling the solution (for example, to room temperature).

Specifically, for example, form I to III crystals of p-toluenesulfonate can be produced by any of the methods described in Examples 13 to 15 which will be described later.

Production of Crystal of Maleate

According to the present invention, a crystal (form I to IV) of maleate of N-{2-chloro-4-[(6,7-dimethoxy-4-quinolyl)oxy]phenyl}-N'-(5-methyl-3-isoxazolyl)urea can be produced by adding an organic solvent and/or water to a maleate of N-{2-chloro-4-[(6,7-dimethoxy-4-quinolyl)oxy]phenyl}-N'-(5-methyl-3-isoxazolyl)urea, dissolving them in each other under heating conditions (for example, at about 100° C.) to prepare a solution, cooling the solution (for example, to room temperature or about 5° C.), and optionally adding a solvent (for example, ethyl acetate) dropwise thereto and further cooling the mixture (for example, to room temperature) to precipitate crystals.

For example, methanol and water, ethanol, N,N-dimethylformamide, or N,N-dimethylacetamide may be mentioned as the organic solvent and/or water.

The maleate of N-{2-chloro-4-[(6,7-dimethoxy-4-quinolyl)oxy]phenyl}-N'-(5-methyl-3-isoxazolyl)urea used in the production of the crystal of the salt may be prepared by adding methanol to N-{2-chloro-4-[(6,7-dimethoxy-4-quinolyl)oxy]phenyl}-N'-(5-methyl-3-isoxazolyl)urea, adding a solution of maleic acid in methanol dropwise thereto, and stirring the mixture. Accordingly, the production process of the crystal of maleate according to the present invention may further include the step of producing the above maleate.

In one preferred embodiment of the present invention, there is provided a process for producing the above form II crystal of maleate, said process comprising the steps of: adding methanol to N-{2-chloro-4-[(6,7-dimethoxy-4-quinolyl)oxy]phenyl}-N'-(5-methyl-3-isoxazolyl)urea, adding a solution of maleic acid in methanol dropwise thereto, stirring the mixture to give a maleate of N-{2-chloro-4-[(6,7-dimethoxy-4-quinolyl)oxy]phenyl}-N'-(5-methyl-3-isoxazolyl)urea, and dissolving the maleate in an organic solvent and/or water, and cooling the solution to precipitate crystals. In this process, ethanol is preferred as the organic solvent and/or water.

Specifically, for example, form I to IV crystals of maleate can be produced by any of the methods described in Examples 16 to 19 which will be described later.

Use of Crystalline Forms of Salts According to the Invention and Pharmaceutical Composition N-{2-Chloro-4-[(6,7-dimethoxy-4-quinolyl)oxy]phenyl}-N'-(5-methyl-3-isoxazolyl)urea has tumor enhancement inhibitory activity in vivo (Pharmacological Test Examples 2, 3, and 4 in WO02/88110). Further, this compound inhibits in vitro the autophosphorylation activity in human KDR intracellular regions caused by stimulation of NIH3T3 cells, which can stably express human KDR, with VEGF (vascular endothelial growth factor) (Pharmacological Test Example 1 in WO 02/88110). Binding of VEGF to KDR, which is present as a receptor of VEGF on cell membranes, causes activation of MAPK (mitogen-activated protein kinase) and the like through autophosphorylation of KDR intracellular regions by tyrosine kinase (Shibuya M, Ito N, Claesson-Welsh L., in Curr. Topics Microbiol Immunol., 237, 59–83 (1999); Abedi, H. and Zachary, I., J. Biol. Chem., 272, 15442–15451 (1997)). The activation of MAPK is known to play an important role in the growth of vascular endothelial cells in angiogenesis (Merenmies, J. et al., Cell Growth & Differ., 83–10 (1997); and Ferrara, N. and Davis- Smyth, T., Endocr. Rev., 18, 4–25 (1997)). Therefore, the above compound has angiogenesis inhibitory activity. It is known that angiogenesis at pathologic sites is deeply involved mainly in diseases, such as tumor, diabetic retinopathy, chronic rheumatism, psoriasis, atherosclerosis, and Kaposi's sarcoma, and metastasis of solid tumors (Folkman, J. Nature Med. 1: 27–31 (1995); Bicknell, R., Harris, A. L. Curr. Opin. Oncol. 8: 60–65 (1996)).

Therefore, N-{2-chloro-4-[(6,7-dimethoxy-4-quinolyl) oxy]phenyl}-N'-(5-methyl-3-isoxazolyl)urea is effective in the therapy of tumors, diabetic retinopathy, chronic rheumatism, psoriasis, atherosclerosis, Kaposi's sarcoma and the like (see application under PCT (PCT/JP02/04279, WO02/88110)). Consequently, crystals of salts of N-{2-chloro-4-[(6,7-dimethoxy-4-quinolyl)oxy]phenyl}-N'-(5-methyl-3-isoxazolyl)urea are effective in the therapy of tumors, diabetic retinopathy, chronic rheumatism, psoriasis, atherosclerosis, Kaposi's sarcoma, exudation type age-related maculopathy, metastasis of solid tumors and the like. Further, the crystals of salts according to the present invention are useful as pharmaceuticals for oral administration.

According to the present invention, there is provided a pharmaceutical composition comprising a crystal of a salt of N-{2-chloro-4-[(6,7-dimethoxy-4-quinolyl)oxy]phenyl}-N'-(5-methyl-3-isoxazolyl)urea and a pharmaceutically acceptable carrier.

The pharmaceutical composition according to the present invention can be used for the therapy of a disease selected from the group consisting of tumors, diabetic retinopathy, chronic rheumatism, psoriasis, atherosclerosis, Kaposi's sarcoma, and exudation type age-related maculopathy. Further, the pharmaceutical composition according to the present invention can be used in the prophylaxis of metastasis or therapy of solid tumors. The pharmaceutical composition according to the present invention is preferably administered orally.

In another embodiment of the present invention, there is provided a method for the therapy of a disease selected from the group consisting of tumors, diabetic retinopathy, chronic rheumatism, psoriasis, atherosclerosis, Kaposi's sarcoma, and exudation type age-related maculopathy, said method comprising the step of administering an effective amount of the crystal of a salt according to the present invention to a mammal patient (for example, a human or a non-human animal).

In a still another embodiment of the present invention, there is provided a method for the prophylaxis of metastasis or therapy of a solid tumor, comprising the step of administering an effective amount of the crystal of a salt according to the present invention to a mammal patient (for example, a human or a non-human animal).

The crystal of a salt of N-{2-chloro-4-[(6,7-dimethoxy-4-quinolyl)oxy]phenyl}-N'-(5-methyl-3-isoxazolyl)urea according to the present invention can be administered to mammal patients either orally or parenterally (for example, rectal administration or percutaneous administration). Therefore, the pharmaceutical composition comprising the crystalline compound according to the present invention as an active ingredient is formulated into suitable dosage forms according to the administration routes.

Specifically, oral preparations include tablets, capsules, powders, granules, and suspensions, and parental preparations include suppositories, tapes, and ointments.

These various preparations may be prepared by conventional methods, for example, with pharmaceutically acceptable carriers, that is, commonly used excipients, disintegrants, binders, lubricants, colorants, and diluents.

Excipients include, for example, lactose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils.

The content of the crystalline compound according to the present invention in the pharmaceutical composition according to the present invention may vary depending upon the dosage form. In general, however, the content is 0.5 to 50% by weight, preferably 1 to 20% by weight, based on the whole composition.

The dose may be appropriately determined in consideration of, for example, the age, weight, sex, difference in diseases, and severity of condition of individual patients, for example, in the range of 0.1 to 100 mg/kg (body weight), preferably in the range of 1 to 50 mg/kg, in terms of the amount of an active ingredient. This dose is administered at a time daily or divided doses of several times daily.

The crystal of a salt according to the present invention may be administered in combination with other medicament. In this case, the crystal of a salt according to the present invention may be administered simultaneously with or after or before the administration of other medicament. For example, when the target disease is a malignant tumor, the tumor can be effectively allowed to disappear by first administering the compound according to the present invention to regress the tumor and then administering a carcinostatic agent. The type and administration intervals of the carcinostatic agent may be determined, for example, depending upon the type of cancer and the condition of patients. This is true of diseases other than the malignant tumor.

Further, according to the present invention, there is provided a therapeutic method comprising the step of bringing the crystal of a salt according to the present invention into contact with tissues causative of diseases (for example, tumor tissues, retinopathy tissues, or rheumatism tissues). The crystalline compound according to the present invention may be brought into contact with tissues causative of diseases, for example, by general administration (for example, oral administration) or local administration (for example, percutaneous administration).

In another embodiment of the present invention, there is provided a method for inhibiting angiogenesis of a target blood vessel, comprising the step of bringing an effective amount of the crystal according to the present invention into contact with vascular endothelial cells of said target blood vessel.

In still another embodiment of the present invention, there is provided use of the crystal according to the present invention, for the manufacture of a pharmaceutical for use in the therapy of a disease selected from the group consisting of tumors, diabetic retinopathy, chronic rheumatism, psoriasis, atherosclerosis, Kaposi's sarcoma, and exudation type age-related maculopathy.

In a further embodiment of the present invention, there is provided use of the crystal according to the present invention, for the manufacture of a pharmaceutical for use in the prophylaxis of metastasis or therapy of solid tumors.

EXAMPLES

The present invention is further illustrated by the following Examples that are not intended as a limitation of the invention.

Production Example

Production of N-{2-chloro-4-[(6,7-dimethoxy-4-quinolyl)oxy]phenyl}-N'-(5-methyl-3-isoxazolyl) urea (1) Step of Nitration:

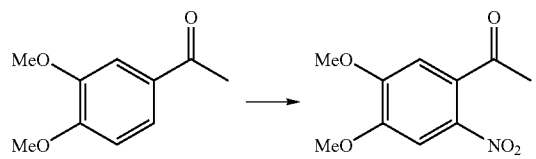

3,4-Dimethoxyacetophenone (1500 g) was dissolved in 170% nitric acid (1400 g) at 5 to 10° C. to prepare a solution which was then slowly added dropwise to a mixed solution composed of 67% nitric acid (8430 g) and sodium nitrite (18 g) at 5 to 10° C. over a period of 2 to 3 hr. After the completion of the dropwise addition, the reaction solution was stirred at 5 to 10° C. for 1 to 2 hr. Cold water (7.5 L) was added thereto, and the mixture was stirred for 30 min. The reaction solution was then filtered and was washed with water (30 L). The filtered product was added to water (7.5 L), and the mixture was neutralized with an aqueous sodium bicarbonate solution, was then filtered, and was washed with water (7 L). The filtered product was dried under the reduced pressure to give 3,4-dimethoxy-6-nitroacetophenone (2164 g, yield 87.9%).

$^1$H-NMR (400 MHz, CDCl$_3$/ppm); δ 2.50 (s, 3H), 3.97 (s, 3H), 3.99 (s, 3H), 6.76 (s, 1H), 7.62 (s, 1H)

(2) Step of Reduction:

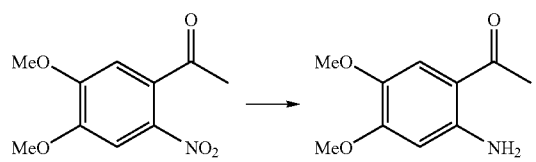

Methanol (5.4 L), acetic acid (433 g), and 5% palladium/carbon (162 g) were added to 3,4-dimethoxy-6-nitroacetophenone (1082 g), and the mixture was stirred under a hydrogen gas pressure of 2 Kg/cm$^2$ at 40° C. for 8 hr. The reaction solution was filtered and was then washed with methanol (1 L). The filtrate was neutralized with an aqueous sodium hydroxide solution and was then concentrated under the reduced pressure. Water (10 L) was added to the concentration, and the mixture was stirred overnight, was then filtered, and was washed with water (7 L). Toluene (4 L) was added to the filtered product, and the mixture was heated to 80° C. and was stirred for 1 hr. The reaction solution was decanted while hot, and the residue was then concentrated under the reduced pressure. The residue was filtered, was washed with toluene (300 mL) and was dried under the reduced pressure to give 2-amino-4,5-dimethoxyacetophenone (576 g, yield 61.4%).

$^1$H-NMR (400 MHz, CDCl$_3$/ppm); δ 2.56 (s, 3H), 3.84 (s, 3H), 3.88 (s, 3H), 6.10 (s, 1H), 7.11 (s, 1H)

(3) Step of Cyclization:

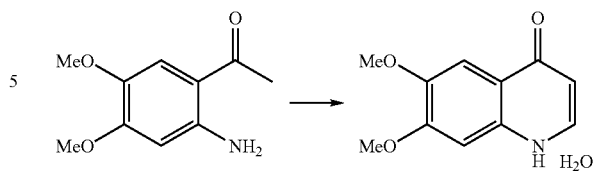

Tetrahydrofuran (THF) (5.3 L) and sodium methoxide (313 g) were added to 2-amino-4,5-dimethoxyacetophenone (337 g), and the mixture was stirred at 20° C. for 30 min. Ethyl formate (858 g) was added to the reaction solution at 0° C., and the mixture was stirred at 20° C. for one hr. Water (480 mL) was added thereto at 0° C., and the mixture was neutralized with 1 N hydrochloric acid. The resultant precipitate was collected by filtration, and the filtered product was slurried in water (2 L) for washing. The slurry was filtered, and the filtered product was then dried under the reduced pressure to give 6,7-dimethoxy-4-quinolone (352 g, yield 81.50%).

$^1$H-NMR (400 MHz, DMSO-d$_6$/ppm); δ 3.81 (s, 3H), 3.84 (s, 3H), 5.94 (d, 1H), 7.01 (s, 1H), 7.43 (s, 1H), 7.76 (d, 1H)

(4) Step of Chlorination:

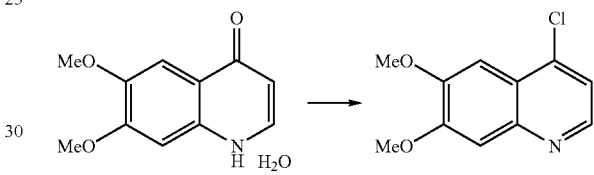

Toluene (3 L) and phosphorus oxychloride (1300 g) were added to 6,7-dimethoxy-4-quinolone (1056 g), and the mixture was heated under reflux with stirring for one hr. The reaction solution was neutralized with an aqueous sodium hydroxide solution at 0° C. The resultant precipitate was collected by filtration and was slurried in water (10 L) for washing. The slurry was filtered, and the filtered product was then dried under the reduced pressure to give 4-chloro-6,7-dimethoxyquinoline (928 g, yield 87.6%).

$^1$H-NMR (400 MHz, DMSO-d$_6$/ppm); δ 3.95 (s, 3H), 3.96 (s, 3H), 7.35 (s, 1H), 7.43 (s, 1H), 7.54 (d, 1H), 8.59 (d, 1H)

(5) Step of Introduction of Phenol Site:

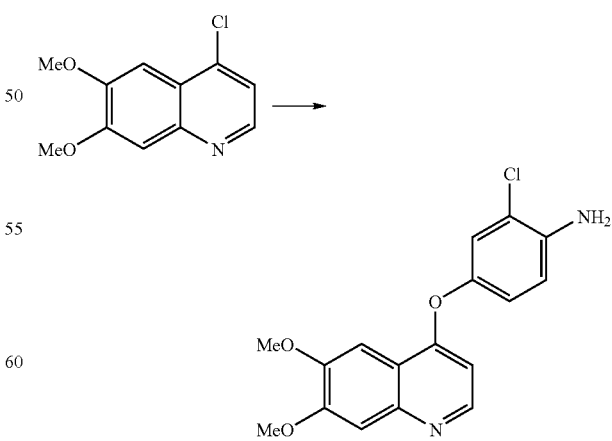

4-Amino-3-chlorophenol·HCl (990 g) was added to N,N-dimethylacetamide (6.6 L). Potassium t-butoxide (1452 g) was added thereto at 0° C., and the mixture was stirred at 20°

C. for 30 min. 4-Chloro-6,7-dimethoxyquinoline (825 g) was added to the reaction solution, and the mixture was then stirred at 115° C. for 5 hr. The reaction solution was cooled to room temperature, water (8.3 L) and methanol (8.3 L) were then added thereto, and the mixture was stirred for 2 hr. The resultant precipitate was collected by filtration, and the filtered product was slurried in water (8.3 L) for washing. The slurry was filtered, and the filtered product was then dried under the reduced pressure to give 4-[(4-amino-3-chlorophenol)oxy]-6,7-dimethoxyquinoline (852 g, yield 69.9%).

$^1$H-NMR (400 MHz, DMSO-$d_6$/ppm); δ 3.92 (s, 3H), 3.93 (s, 3H), 5.41 (s, 2H), 6.41 (d, 1H), 6.89 (d, 1H), 6.98 (dd, 1H), 7.19 (d, 1H), 7.36 (s, 1H), 7.48 (s, 1H), 8.43 (d, 1H)

(6) Step of Conversion to Urea Compound:

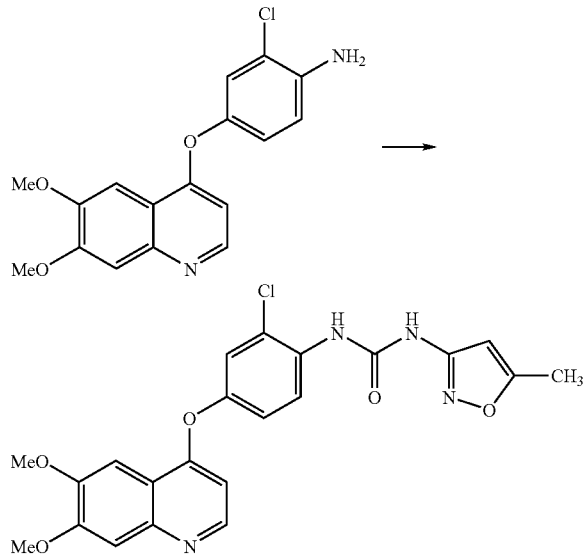

Phenyl chlorocarbonate (601 g) was added dropwise to 3-amino-5-methylisoxazole (377 g), pyridine (1215 g), and N,N-dimethylacetamide (4 L) at 0° C., and the mixture was stirred at 20° C. for 2 hr. 4-[(4-Amino-3-chlorophenol)oxy]-6,7-dimethoxyquinoline (847 g) was added to the reaction solution, and the mixture was stirred at 80° C. for 5 hr. The reaction solution was cooled to 5° C. Thereafter, methanol (8.5 L) and water (8.5 L) were added thereto, and the mixture was neutralized with an aqueous sodium hydroxide solution. The resultant precipitate was collected by filtration, and the filtered product was slurried in water (8.5 L) for washing. The slurry was filtered, and the filtered product was then dried under the reduced pressure to give N-{2-chloro-4-[(6,7-dimethoxy-4-quinolyl)oxy]phenyl}-N'-(5-methyl-3-isoxazolyl)urea (1002 g, yield 86.1%).

$^1$H-NMR (400 MHz, DMSO-$d_6$/ppm); δ 2.37 (s, 3H), 3.92 (s, 3H), 3.94 (s, 3H), 6.50 (s, 1H), 6.54 (d, 1H), 7.26 (dd, 1H), 7.39 (s, 1H), 7.48 (s, 1H), 7.5 (d, 1H), 8.23 (d, 1H), 8.49 (d, 1H), 8.77 (s, 1H), 10.16 (s, 1H)

Production of Crystal and Measurement of Properties Thereof

Crystals were produced from N-{2-chloro-4-[(6,7-dimethoxy-4-quinolyl)oxy]phenyl}-N'-(5-methyl-3-isoxazolyl)urea, produced in the above-described Production Example, as described in Examples which will be described later, and the properties of the crystals were measured by the following measuring methods 1 to 4.

Measuring Method 1: Powder X-Ray Diffractometry

X-ray diffraction patterns of crystals were taken using Cu-Kα radiation (40 kV, 40 mA, λ=1.541 angstroms) with a powder X-ray diffraction apparatus (X-ray diffraction RINT DMAX-2000, manufactured by Rigaku Industrial Corporation) (scanning speed: 5 degrees/min, scanning range: 5.000 to 40.000 degrees, filter: Kβ filter). Based on powder X-ray diffraction patterns thus obtained, peak positions and relative intensity (%) were determined for peaks with a relative intensity of not less than 20%.

Measuring Method 2: Differential Scanning Calorimetry

The differential scanning calory of crystals were determined with an input compensation type differential scanning calory analyzer (Pyris 1, manufactured by PERKIN ELMER).

A sample was first packed into an aluminum sample container which was then placed in a heating furnace part (sample side) of the analyzer. An empty aluminum sample container was provided as a reference and was placed in the heating furnace part (reference side). The heating furnace part was then heated according to a predetermined temperature control program, and a change in quantity of heat attributable to the temperature change was continuously measured and recorded. During the measurement, dry nitrogen was introduced at a constant flow rate into the heating furnace. Based on the differential scanning calorimetrically measured charts thus obtained, exothermic/endothermic peaks for each crystal were analyzed.

Measuring Method 3: Thermogravimetry

The thermogravimetry of crystals was carried out with a thermogravimetric analyzer (thermobalance: hang type) (TGA7, manufactured by PERKIN ELMER).

A sample was first packed in a platinum sample container which was then set in the analyzer at its predetermined position. The heating furnace part was then heated according to a predetermined temperature control program, and a change in mass of the sample attributable to the temperature change was continuously measured and recorded by the analyzer. The relative value (%) of the mass change attributable to heating to the amount of the sample used was determined from the mass-time curve thus obtained to provide a thermogravimetrically measured chart.

Measurement Method 4: Water Content

The water content of crystals was measured by coulometric titration using the Karl Fischer method (Japanese Pharmacopeia).

Production of crystal of salt of N-{2-chloro-4-[(6,7-dimethoxy-4-quinolyl)oxy]phenyl}-N'-(5-methyl-3-isoxazolyl)urea Example 1

Production of Form I Crystal of Hydrochloride

N-{2-Chloro-4-[(6,7-dimethoxy-4-quinolyl)oxy]phenyl}-N'-(5-methyl-3-isoxazolyl)urea (1000 g) produced according to Production Example was added to and was completely dissolved in N,N-dimethylformamide (7 L) at 60° C. The solution was allowed to cool to room temperature, and 12 N hydrochloric acid (202 mL), ethanol (28 L), and water (2.8 L) were then added thereto, and the mixture was stirred at room temperature. After the precipitation of crystals was confirmed, the solution was stirred at 5° C. overnight. The resultant precipitate was collected by filtration, and the filtered product was then slurried in ethanol (5 L) for washing. The slurry was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea hydrochloride (836 g, yield 74.7%).

$^1$H-NMR (400 MHz, DMSO-d$_6$/ppm); δ 2.37 (s, 3H), 4.02 (s, 3H), 4.03 (s, 3H), 6.50 (s, 1H), 6.95 (d, 1H), 7.42 (dd, 1H), 7.69 (s, 1H), 7.70 (s, 1H), 7.72 (d, 1H), 8.32 (d, 1H), 8.79 (d, 1H), 9.01 (s, 1H), 10.38 (s, 1H)

The crystal thus obtained was analyzed by the above-described powder X-ray diffractometry, differential scanning calorimetry, and thermogravimetric measurement.

Table 1 shows positions and relative intensities (%) of peaks with a relative intensity of not less than 20% for the crystal.

FIG. 1 shows a differential scanning calorimetrically measured chart for the crystal with endothermic peaks at temperatures around 120° C. and 190° C. FIG. 2 is a thermogravimetrically measured chart for the crystal.

TABLE 1

| Diffraction angle (2θ) | Relative intensity (>20%) |
|---|---|
| 8.76 | 22 |
| 11.47 | 100 |
| 15.28 | 21 |
| 17.16 | 21 |
| 17.53 | 23 |
| 18.80 | 21 |
| 20.02 | 25 |
| 22.59 | 35 |
| 23.02 | 37 |
| 25.32 | 29 |
| 25.43 | 23 |
| 26.27 | 36 |
| 26.63 | 32 |
| 27.00 | 29 |
| 28.57 | 28 |

Example 2

Production of form II Crystal of Hydrochloride

N-{2-Chloro-4-[(6,7-dimethoxy-4-quinolyl)oxy]phenyl}-N'-(5-methyl-3-isoxazolyl)urea (2 g) produced in Production Example was added to and was completely dissolved in N,N-dimethylformamide (10 mL) at 80° C. The solution was allowed to cool to room temperature, and 12 N hydrochloric acid (202 mL) was then added thereto, followed by stirring for one hr. The reaction solution was heated to 80° C., 1-propanol (60 mL) of 80° C. was added thereto, and the mixture was stirred at 80° C. After the precipitation of crystals was confirmed, the solution was cooled to 5° C. and was stirred at that temperature overnight. The resultant precipitate was collected by filtration, and the filtered product was dried under the reduced pressure to give a form II crystal of N-{2-chloro-4-[(6,7-dimethoxy-4-quinolyl)oxy]phenyl}-N'-(5-methyl-3-isoxazolyl)urea hydrochloride (1.81 g, yield 83.8%).

The crystal thus obtained was analyzed by the above-described powder X-ray diffractometry, differential scanning calorimetry, and thermogravimetric measurement.

Table 2 shows positions and relative intensities (%) of peaks with a relative intensity of not less than 20% for the crystal.

FIG. 3 shows a differential scanning calorimetrically measured chart for the crystal with an endothermic peak at a temperature around 220° C. FIG. 4 is a thermogravimetrically measured chart for the crystal.

TABLE 2

| Diffraction angle (2θ) | Relative intensity (>20%) |
|---|---|
| 9.37 | 26 |
| 12.15 | 37 |
| 12.54 | 32 |
| 12.88 | 29 |
| 21.32 | 31 |
| 21.48 | 30 |
| 21.82 | 27 |
| 22.13 | 37 |
| 23.16 | 23 |
| 24.12 | 37 |
| 25.22 | 100 |
| 25.95 | 31 |

Example 3

Production of Form III Crystal of Hydrochloride

N-{2-Chloro-4-[(6,7-dimethoxy-4-quinolyl)oxy]phenyl}-N'-(5-methyl-3-isoxazolyl)urea (2 g) produced in Production Example was added to 1-butanol (120 mL), 12 N hydrochloric acid (202 mL) was added thereto, and the mixture was stirred for one hr. The reaction solution was heated under reflux with stirring. After complete dissolution was confirmed, the solution was cooled to room temperature and was stirred at that temperature overnight. The resultant precipitate was filtered, and the filtered product was dried under the reduced pressure to give a form III crystal of N-{2-chloro-4-[(6,7-dimethoxy-4-quinolyl)oxy]phenyl}-N'-(5-methyl-3-isoxazolyl)urea hydrochloride (1.81 g, yield 84.0%).

The crystal thus obtained was analyzed by the above-described powder X-ray diffractometry, differential scanning calorimetry, and thermogravimetric measurement.

Table 3 shows positions and relative intensities (%) of peaks with a relative intensity of not less than 20% for the crystal.

FIG. 5 shows a differential scanning calorimetrically measured chart for the crystal with endothermic peaks at temperatures around 160° C. and 220° C. FIG. 6 is a thermogravimetrically measured chart for the crystal.

TABLE 3

| Diffraction angle (2θ) | Relative intensity (>20%) |
|---|---|
| 5.07 | 39 |
| 7.20 | 100 |
| 11.42 | 59 |
| 14.58 | 41 |
| 20.43 | 42 |
| 21.86 | 59 |
| 23.75 | 52 |
| 24.59 | 53 |
| 24.71 | 42 |
| 25.18 | 61 |
| 25.34 | 60 |
| 26.01 | 61 |

Example 4

Production of Form I Crystal of Nitrate

N-{2-Chloro-4-[(6,7-dimethoxy-4-quinolyl)oxy]phenyl}-N'-(5-methyl-3-isoxazolyl)urea (2.0 g) produced in Production Example was added to methanol (40 mL), 70% nitric acid (1.2 g) was added dropwise thereto, and the mixture was stirred at room temperature for 2 hr. The resultant precipitate was collected by filtration, and the filtered product was then dried under the reduced pressure. The powder thus obtained was stirred in methanol (200 mL) and water (100 mL) under reflux for complete dissolution of the powder. The solution was then cooled to 5° C. and was stirred at that temperature overnight. The resultant precipitate was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea nitrate (2.0 g, yield 88.0%).

$^1$H-NMR (400 MHz, DMSO-d$_6$/ppm); δ 2.37 (s, 3H), 4.03 (s, 3H), 4.05 (s, 3H), 6.50 (s, 1H), 7.00 (d, 1H), 7.43 (dd, 1H), 7.53 (s, 1H), 7.72 (d, 1H), 7.74 (s, 1H), 8.36 (d, 1H), 8.84 (d, 1H), 8.87 (s, 1H), 10.23 (s, 1H)

The crystal thus obtained was analyzed by the above-described powder X-ray diffractometry, differential scanning calorimetry, and thermogravimetric measurement.

Table 4 shows positions and relative intensities (%) of peaks with a relative intensity of not less than 20% for the crystal.

FIG. 7 shows a differential scanning calorimetrically measured chart for the crystal with an endothermic peak at a temperature around 220° C. FIG. 8 is a thermogravimetrically measured chart for the crystal.

TABLE 4

| Diffraction angle (2θ) | Relative intensity (>20%) |
|---|---|
| 7.23 | 79 |
| 9.50 | 67 |
| 10.91 | 100 |
| 11.89 | 62 |
| 17.95 | 33 |
| 18.93 | 90 |
| 19.80 | 41 |
| 21.90 | 51 |
| 23.64 | 71 |
| 23.83 | 90 |
| 24.43 | 36 |
| 25.51 | 91 |
| 26.12 | 95 |
| 27.40 | 56 |
| 27.56 | 60 |
| 28.34 | 81 |
| 28.95 | 69 |
| 29.06 | 65 |

Example 5

Production of Form II Crystal of Nitrate

N-{2-Chloro-4-[(6,7-dimethoxy-4-quinolyl)oxy]phenyl}-N'-(5-methyl-3-isoxazolyl)urea (2.0 g) produced in Production Example was added to methanol (40 mL), 70% nitric acid (1.2 g) was added dropwise thereto, and the mixture was stirred at room temperature for 2 hr. The resultant precipitate was collected by filtration, and the filtered product was then dried under the reduced pressure. The resultant powder was stirred in N,N-dimethylformamide (10 mL) at 100° C. for complete dissolution of the powder. The solution was then cooled to room temperature, ethyl acetate (20 mL) was added dropwise thereto, and the mixture was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea nitrate (2.0 g, yield 91.0%).

The crystal thus obtained was analyzed by the above-described powder X-ray diffractometry, differential scanning calorimetry, and thermogravimetric measurement.

Table 5 shows positions and relative intensities (%) of peaks with a relative intensity of not less than 20% for the crystal.

FIG. 9 shows a differential scanning calorimetrically measured chart for the crystal with an endothermic peak at a temperature around 120° C. and an exothermic peak at a temperature around 220° C. FIG. 10 is a thermogravimetrically measured chart for the crystal.

TABLE 5

| Diffraction angle (2θ) | Relative intensity (>20%) |
|---|---|
| 9.08 | 51 |
| 11.78 | 53 |
| 23.33 | 44 |
| 23.45 | 46 |
| 23.66 | 47 |
| 24.80 | 50 |
| 25.91 | 72 |
| 26.22 | 94 |
| 26.49 | 100 |

Example 6

Production of Form I Crystal of Sulfate

N-{2-Chloro-4-[(6,7-dimethoxy-4-quinolyl)oxy]phenyl}-N'-(5-methyl-3-isoxazolyl)urea (2.0 g) produced in Production Example was added to methanol (53 mL), concentrated sulfuric acid (concentration 98%) (1.3 g) was added dropwise thereto, and the mixture was stirred at room temperature for 4 hr. The resultant precipitate was collected by filtration, and the filtered product was then dried under the reduced pressure. The powder thus obtained was stirred in acetonitrile (200 mL) and water (40 mL) under reflux for complete dissolution. The solution was then cooled to 5° C. and was stirred at that temperature overnight. The resultant precipitate was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea sulfate (1.9 g, yield 78.0%).

$^1$H-NMR (400 MHz, DMSO-d$_6$/ppm); δ 2.37 (s, 3H), 4.02 (s, 3H), 4.04 (s, 3H), 6.50 (s, 1H), 6.96 (d, 1H), 7.42 (dd, 1H), 7.55 (s, 1H), 7.71 (d, 1H), 7.72 (s, 1H), 8.35 (d, 1H), 8.81 (d, 1H), 8.87 (s, 1H), 10.22 (s, 1H)

The crystal thus obtained was analyzed by the above-described powder X-ray diffractometry, differential scanning calorimetry, and thermogravimetric measurement.

Table 6 shows positions and relative intensities (%) of peaks with a relative intensity of not less than 200% for the crystal.

FIG. 11 shows a differential scanning calorimetrically measured chart for the crystal with an endothermic peak at a temperature around 200° C. FIG. 12 is a thermogravimetrically measured chart for the crystal.

TABLE 6

| Diffraction angle (2θ) | Relative intensity (>20%) |
| --- | --- |
| 8.71 | 56 |
| 9.40 | 63 |
| 9.56 | 46 |
| 12.30 | 81 |
| 13.98 | 92 |
| 14.41 | 56 |
| 15.13 | 97 |
| 17.28 | 52 |
| 21.40 | 38 |
| 21.96 | 100 |
| 25.39 | 40 |
| 25.61 | 34 |
| 26.90 | 35 |

Example 7

Production of Form II Crystal of Sulfate

N-{2-Chloro-4-[(6,7-dimethoxy-4-quinolyl)oxy]phenyl}-N'-(5-methyl-3-isoxazolyl)urea (2.0 g) produced in Production Example was added to methanol (53 mL), concentrated sulfuric acid (concentration 98%) (1.3 g) was added dropwise thereto, and the mixture was stirred at room temperature for 4 hr. The resultant precipitate was collected by filtration, and the filtered product was then dried under the reduced pressure. The powder thus obtained was stirred in N,N-dimethylformamide (20 mL) at 140° C. for complete dissolution. The solution was then cooled to 5° C. and was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea sulfate (1.0 g, yield 41.0%).

The crystal thus obtained was analyzed by the above-described powder X-ray diffractometry, differential scanning calorimetry, and thermogravimetric measurement.

Table 7 shows positions and relative intensities (%) of peaks with a relative intensity of not less than 20% for the crystal.

FIG. 13 shows a differential scanning calorimetrically measured chart for the crystal with an endothermic peak at a temperature around 180° C. FIG. 14 is a thermogravimetrically measured chart for the crystal.

TABLE 7

| Diffraction angle (2θ) | Relative intensity (>20%) |
| --- | --- |
| 6.19 | 76 |
| 8.09 | 33 |
| 12.35 | 78 |
| 13.08 | 33 |
| 16.65 | 100 |
| 18.38 | 38 |
| 18.52 | 45 |
| 21.12 | 29 |
| 22.07 | 59 |
| 22.17 | 69 |
| 23.03 | 39 |
| 23.94 | 38 |
| 24.13 | 34 |
| 24.78 | 32 |
| 25.68 | 42 |
| 26.54 | 35 |
| 27.02 | 33 |
| 28.14 | 33 |

Example 8

Production of Form I Crystal of Methanesulfonate

N-{2-Chloro-4-[(6,7-dimethoxy-4-quinolyl)oxy]phenyl}-N'-(5-methyl-3-isoxazolyl)urea (2.0 g) produced in Production Example was added to methanol (50 mL), methanesulfonic acid (1.3 g) was added dropwise thereto, and the mixture was stirred at room temperature for 4 hr. The resultant precipitate was collected by filtration, and the filtered product was then dried under the reduced pressure. The powder thus obtained was stirred in N,N-dimethylacetamide (10 mL) at 80° C. for complete dissolution. The solution was then cooled to room temperature, acetonitrile (30 mL) was added dropwise thereto, and the mixture was cooled to 5° C. and was stirred at that temperature overnight. The resultant precipitate was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea methanesulfonate (1.7 g, yield 69.0%).

$^1$H-NMR (400 MHz, DMSO-$d_6$/ppm); δ 2.34 (s, 3H), 2.37 (s, 3H), 4.03 (s, 3H), 4.05 (s, 3H), 6.50 (s, 1H), 7.00 (d, 1H), 7.42 (dd, 1H), 7.59 (s, 1H), 7.72 (d, 1H), 7.74 (s, 1H), 8.36 (d, 1H), 8.83 (d, 1H), 8.87 (s, 1H), 10.23 (s, 1H)

The crystal thus obtained was analyzed by the above-described powder X-ray diffractometry, differential scanning calorimetry, and thermogravimetric measurement.

Table 8 shows positions and relative intensities (%) of peaks with a relative intensity of not less than 20% for the crystal.

FIG. 15 shows a differential scanning calorimetrically measured chart for the crystal with an endothermic peak at a temperature around 210° C. FIG. 16 is a thermogravimetrically measured chart for the crystal.

TABLE 8

| Diffraction angle (2θ) | Relative intensity (>20%) |
| --- | --- |
| 5.36 | 81 |
| 8.04 | 95 |
| 9.25 | 78 |
| 18.38 | 100 |
| 18.83 | 49 |
| 19.73 | 53 |
| 20.42 | 49 |
| 21.30 | 79 |
| 22.20 | 92 |
| 22.62 | 41 |
| 24.25 | 44 |
| 24.72 | 66 |
| 25.42 | 54 |
| 26.27 | 59 |
| 26.97 | 47 |

Example 9

Production of Form II Crystal of Methanesulfonate

N-{2-Chloro-4-[(6,7-dimethoxy-4-quinolyl)oxy]phenyl}-N'-(5-methyl-3-isoxazolyl)urea (2.0 g) produced in Production Example was added to methanol (50 mL), methanesulfonic acid (1.3 g) was added dropwise thereto, and the mixture was stirred at room temperature for 4 hr. The resultant precipitate was collected by filtration, and the filtered product was then dried under the reduced pressure. The powder thus obtained was stirred in ethanol (120 mL) under reflux for complete dissolution. The solution was then cooled to 5° C. and was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea methanesulfonate (1.9 g, yield 80.0%).

The crystal thus obtained was analyzed by the above-described powder X-ray diffractometry, differential scanning calorimetry, and thermogravimetric measurement.

Table 9 shows positions and relative intensities (%) of peaks with a relative intensity of not less than 20% for the crystal.

FIG. 17 shows a differential scanning calorimetrically measured chart for the crystal with an endothermic peak at temperatures around 160° C. and 240° C. FIG. 18 is a thermogravimetrically measured chart for the crystal.

TABLE 9

| Diffraction angle (2θ) | Relative intensity (>20%) |
|---|---|
| 9.22 | 100 |
| 17.35 | 54 |
| 18.78 | 58 |
| 21.64 | 56 |
| 23.03 | 45 |
| 23.12 | 45 |
| 24.09 | 49 |
| 24.31 | 60 |
| 25.48 | 81 |
| 25.67 | 79 |
| 26.27 | 79 |
| 26.47 | 84 |
| 26.64 | 78 |

Example 10

Production of Form III Crystal of Methanesulfonate

N-{2-Chloro-4-[(6,7-dimethoxy-4-quinolyl)oxy]phenyl}-N'-(5-methyl-3-isoxazolyl)urea (2.0 g) produced in Production Example was added to methanol (50 mL), methanesulfonic acid (1.3 g) was added dropwise thereto, and the mixture was stirred at room temperature for 4 hr. The resultant precipitate was collected by filtration, and the filtered product was then dried under the reduced pressure. The powder thus obtained was stirred in N,N-dimethylformamide (5 mL) at 100° C. for complete dissolution. The solution was then cooled to 5° C. and the mixture was stirred at that temperature overnight. The resultant precipitate was filtered, and the filtered product was then dried under the reduced pressure to give a form III crystal of N-{2-chloro-4-[(6,7-dimethoxy-4-quinolyl)oxy]phenyl}-N'-(5-methyl-3-isoxazolyl)urea methanesulfonate (1.5 g, yield 61.0%).

The crystal thus obtained was analyzed by the above-described powder X-ray diffractometry, differential scanning calorimetry, and thermogravimetric measurement.

Table 10 shows positions and relative intensities (%) of peaks with a relative intensity of not less than 20% for the crystal.

FIG. 19 shows a differential scanning calorimetrically measured chart for the crystal with an endothermic peak at temperatures around 160° C. and 240° C. FIG. 20 is a thermogravimetrically measured chart for the crystal.

TABLE 10

| Diffraction angle (2θ) | Relative intensity (>20%) |
|---|---|
| 4.82 | 41 |
| 6.35 | 46 |
| 16.33 | 38 |
| 17.48 | 42 |
| 18.81 | 39 |
| 20.58 | 37 |
| 22.73 | 42 |
| 22.98 | 43 |
| 23.10 | 42 |
| 24.59 | 80 |
| 24.67 | 89 |
| 24.93 | 100 |
| 25.58 | 42 |

Example 11

Production of Form IV Crystal of Methanesulfonate

N-{2-Chloro-4-[(6,7-dimethoxy-4-quinolyl)oxy]phenyl}-N'-(5-methyl-3-isoxazolyl)urea (2.0 g) produced in Production Example was added to methanol (50 mL), methanesulfonic acid (1.3 g) was added dropwise thereto, and the mixture was stirred at room temperature for 4 hr. The resultant precipitate was collected by filtration, and the filtered product was then dried under the reduced pressure. The powder thus obtained was stirred in acetonitrile (40 mL) and methanol (10 mL) under reflux for complete dissolution. The solution was then cooled to 5° C. and the mixture was stirred at that temperature overnight. The resultant precipitate was filtered, and the filtered product was then dried under the reduced pressure to give a form IV crystal of N-{2-chloro-4-[(6,7-dimethoxy-4-quinolyl)oxy]phenyl}-N'-(5-methyl-3-isoxazolyl)urea methanesulfonate (1.5 g, yield 62.0%).

The crystal thus obtained was analyzed by the above-described powder X-ray diffractometry, differential scanning calorimetry, and thermogravimetric measurement.

Table 11 shows positions and relative intensities (%) of peaks with a relative intensity of not less than 20% for the crystal.

FIG. 21 shows a differential scanning calorimetrically measured chart for the crystal with an endothermic peak at temperatures around 120° C., 160° C. and 240° C. FIG. 22 is a thermogravimetrically measured chart for the crystal.

TABLE 11

| Diffraction angle (2θ) | Relative intensity (>20%) |
|---|---|
| 7.70 | 100 |
| 9.21 | 45 |
| 9.98 | 48 |
| 15.32 | 92 |
| 15.85 | 66 |
| 16.77 | 41 |
| 22.02 | 48 |
| 22.14 | 52 |
| 23.35 | 48 |
| 25.34 | 39 |
| 26.62 | 60 |
| 26.76 | 55 |

Example 12

Production of Form V Crystal of Methanesulfonate

N-{2-Chloro-4-[(6,7-dimethoxy-4-quinolyl)oxy]phenyl}-N'-(5-methyl-3-isoxazolyl)urea (2.0 g) produced in Production Example was added to methanol (50 mL), methanesulfonic acid (1.3 g) was added dropwise thereto, and the mixture was stirred at room temperature for 4 hr. The resultant precipitate was collected by filtration, and the filtered product was then dried under the reduced pressure. The powder thus obtained was stirred in N,N-dimethylformamide (5 mL) at 100° C. for complete dissolution. The solution was then cooled to room temperature. Ethyl acetate (20 mL) was added dropwise thereto, and the mixture was stirred at room temperature overnight. The resultant precipitate was filtered, and the filtered product was then dried under the reduced pressure to give a form V crystal of N-{2-chloro-4-[(6,7-dimethoxy-4-quinolyl)oxy]phenyl}-N'-(5-methyl-3-isoxazolyl)urea methanesulfonate (2.0 g, yield 82.0%).

The crystal thus obtained was analyzed by the above-described powder X-ray diffractometry, differential scanning calorimetry, and thermogravimetric measurement.

Table 12 shows positions and relative intensities (%) of peaks with a relative intensity of not less than 20% for the crystal.

FIG. 23 shows a differential scanning calorimetrically measured chart for the crystal with an endothermic peak at a temperature around 160° C. FIG. 24 is a thermogravimetrically measured chart for the crystal.

TABLE 12

| Diffraction angle (2θ) | Relative intensity (>20%) |
|---|---|
| 6.67 | 78 |
| 18.23 | 44 |
| 18.49 | 43 |
| 19.57 | 65 |
| 19.97 | 52 |
| 20.47 | 44 |
| 20.71 | 47 |
| 20.99 | 48 |
| 22.24 | 51 |
| 22.51 | 53 |
| 22.85 | 63 |
| 23.16 | 100 |
| 24.02 | 63 |
| 24.38 | 85 |
| 24.63 | 77 |
| 24.95 | 66 |

Example 13

Production of Form I Crystal of p-toluenesulfonate

N-{2-Chloro-4-[(6,7-dimethoxy-4-quinolyl)oxy]phenyl}-N'-(5-methyl-3-isoxazolyl)urea (2.0 g) produced in Production Example was added to acetonitrile (27 mL), a solution of p-toluenesulfonic acid monohydrate (2.5 g) in acetonitrile (27 mL) was added dropwise thereto, and the mixture was stirred at room temperature for 3 hr. The resultant precipitate was collected by filtration and the filtered product was then dried under the reduced pressure. The powder thus obtained was stirred in methanol (70 mL) and water (40 mL) under reflux for complete dissolution. The solution was then cooled to room temperature and was stirred at that temperature overnight. The resultant precipitate was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea p-toluenesulfonate (2.3 g, yield 84.0%).

$^1$H-NMR (400 MHz, DMSO-$d_6$/ppm); δ 2.27 (s, 3H), 2.37 (s, 3H), 4.03 (s, 3H), 4.04 (s, 3H), 6.50 (s, 1H), 7.00 (d, 1H), 7.09 (s, 1H), 7.11 (s, 1H), 7.43 (dd, 1H), 7.46 (d, 1H), 7.48 (d, 1H), 7.55 (s, 1H), 7.72 (d, 1H), 7.74 (s, 1H), 8.36 (d, 1H), 8.84 (d, 1H), 8.88 (s, 1H), 10.23 (s, 1H)

The crystal thus obtained was analyzed by the above-described powder X-ray diffractometry, differential scanning calorimetry, and thermogravimetric measurement.

Table 13 shows positions and relative intensities (%) of peaks with a relative intensity of not less than 20% for the crystal.

FIG. 25 shows a differential scanning calorimetrically measured chart for the crystal with endothermic peaks at temperatures around 120° C. and 180° C. FIG. 26 is a thermogravimetrically measured chart for the crystal.

TABLE 13

| Diffraction angle (2θ) | Relative intensity (>20%) |
|---|---|
| 4.92 | 77 |
| 9.48 | 65 |
| 15.74 | 36 |
| 16.17 | 82 |
| 16.85 | 68 |
| 17.19 | 30 |
| 17.55 | 45 |
| 19.03 | 100 |
| 21.19 | 49 |
| 21.36 | 44 |
| 21.80 | 46 |
| 22.30 | 26 |
| 23.75 | 33 |
| 23.93 | 38 |
| 24.36 | 56 |
| 25.27 | 76 |
| 25.78 | 43 |
| 26.88 | 83 |
| 28.15 | 29 |
| 28.41 | 41 |

Example 14

Production of Form II Crystal of p-toluenesulfonate

N-{2-Chloro-4-[(6,7-dimethoxy-4-quinolyl)oxy]phenyl}-N'-(5-methyl-3-isoxazolyl)urea (2.0 g) produced in Production Example was added to acetonitrile (27 mL), a solution of p-toluenesulfonic acid monohydrate (2.5 g) in acetonitrile (27 mL) was added dropwise thereto, and the mixture was stirred at room temperature for 3 hr. The resultant precipitate was collected by filtration and the filtered product was then dried under the reduced pressure. The powder thus obtained was stirred in N,N-dimethylacetamide (10 mL) at 100° C. for complete dissolution. The solution was then cooled to room temperature, and water (10 mL) was added dropwise thereto. The mixture was cooled to 5° C. and was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea p-toluenesulfonate (2.3 g, yield 84.0%).

The crystal thus obtained was analyzed by the above-described powder X-ray diffractometry, differential scanning calorimetry, and thermogravimetric measurement.

Table 14 shows positions and relative intensities (%) of peaks with a relative intensity of not less than 20% for the crystal.

FIG. 27 shows a differential scanning calorimetrically measured chart for the crystal with endothermic peaks at temperatures around 120° C. and 180° C. FIG. 28 is a thermogravimetrically measured chart for the crystal.

TABLE 14

| Diffraction angle (2θ) | Relative intensity (>20%) |
|---|---|
| 4.86 | 82 |
| 9.42 | 54 |
| 12.45 | 28 |
| 15.83 | 44 |
| 16.16 | 37 |
| 16.74 | 39 |
| 17.31 | 38 |
| 17.62 | 42 |
| 18.93 | 67 |
| 21.17 | 51 |
| 21.82 | 25 |
| 22.39 | 26 |
| 24.03 | 50 |
| 24.31 | 39 |
| 25.57 | 82 |
| 26.01 | 35 |
| 27.16 | 100 |
| 28.48 | 50 |

TABLE 15

| Diffraction angle (2θ) | Relative intensity (>20%) |
|---|---|
| 4.94 | 76 |
| 9.53 | 78 |
| 15.69 | 59 |
| 16.22 | 68 |
| 16.80 | 61 |
| 16.98 | 71 |
| 17.11 | 65 |
| 17.51 | 81 |
| 19.14 | 93 |
| 21.36 | 54 |
| 21.89 | 50 |
| 22.25 | 43 |
| 23.31 | 45 |
| 23.44 | 50 |
| 23.71 | 45 |
| 24.03 | 56 |
| 24.45 | 64 |
| 24.86 | 66 |
| 25.03 | 72 |
| 25.21 | 72 |
| 25.48 | 73 |
| 25.59 | 69 |
| 25.92 | 59 |
| 26.04 | 58 |
| 26.61 | 100 |
| 27.11 | 57 |
| 28.04 | 47 |
| 28.18 | 48 |
| 28.55 | 66 |
| 28.85 | 41 |

Example 15

Production of Form III Crystal of p-toluenesulfonate

N-{2-Chloro-4-[(6,7-dimethoxy-4-quinolyl)oxy]phenyl}-N'-(5-methyl-3-isoxazolyl)urea (2.0 g) produced in Production Example was added to acetonitrile (27 mL), a solution of p-toluenesulfonic acid monohydrate (2.5 g) in acetonitrile (27 mL) was added dropwise thereto, and the mixture was stirred at room temperature for 3 hr. The resultant precipitate was collected by filtration and the filtered product was then dried under the reduced pressure. The powder thus obtained was stirred in methanol (160 mL) under reflux for complete dissolution. The solution was then cooled to room temperature and was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea p-toluenesulfonate (2.0 g, yield 74.0%).

The crystal thus obtained was analyzed by the above-described powder X-ray diffractometry, differential scanning calorimetry, and thermogravimetric measurement.

Table 15 shows positions and relative intensities (%) of peaks with a relative intensity of not less than 20% for the crystal.

FIG. 29 shows a differential scanning calorimetrically measured chart for the crystal with endothermic peaks at temperatures around 120° C. and 190° C. FIG. 30 is a thermogravimetrically measured chart for the crystal.

Example 16

Production of Form I Crystal of Maleate

N-{2-Chloro-4-[(6,7-dimethoxy-4-quinolyl)oxy]phenyl}-N'-(5-methyl-3-isoxazolyl)urea (2.0 g) produced in Production Example was added to methanol (27 mL), a solution of maleic acid (1.5 g) in methanol (27 mL) was added dropwise thereto, and the mixture was stirred at room temperature for 4 hr. The resultant precipitate was collected by filtration, and the filtered product was then dried under the reduced pressure. The powder thus obtained was stirred in methanol (100 mL) and water (50 mL) under reflux for complete dissolution. The solution was then cooled to room temperature and was stirred at that temperature overnight. The resultant precipitate was filtered, and the filtered product was then dried under the reduced pressure to give a form I crystal of N-{2-chloro-4-[(6,7-dimethoxy-4-quinolyl)oxy]phenyl}-N'-(5-methyl-3-isoxazolyl)urea maleate (1.7 g, yield 68.0%).

$^1$H-NMR (400 MHz, DMSO-$d_6$/ppm); δ 2.37 (s, 3H), 3.96 (s, 3H), 3.98 (s, 3H), 6.19 (s, 2H), 6.50 (s, 1H), 6.71 (d, 1H), 7.32 (dd, 1H), 7.44 (s, 1H), 7.58 (s, 1H), 7.59 (d, 1H), 8.28 (d, 1H), 8.62 (d, 1H), 8.81 (s, 1H), 10.18 (s, 1H)

The crystal thus obtained was analyzed by the above-described powder X-ray diffractometry, differential scanning calorimetry, and thermogravimetric measurement.

Table 16 shows positions and relative intensities (%) of peaks with a relative intensity of not less than 20% for the crystal.

FIG. 31 shows a differential scanning calorimetrically measured chart for the crystal with an endothermic peak at a temperature around 190° C. FIG. 32 is a thermogravimetrically measured chart for the crystal.

TABLE 16

| Diffraction angle (2θ) | Relative intensity (>20%) |
|---|---|
| 6.30 | 22 |
| 9.82 | 29 |
| 11.68 | 31 |
| 14.25 | 49 |
| 15.27 | 35 |
| 15.66 | 100 |
| 18.86 | 84 |
| 21.85 | 50 |
| 22.12 | 78 |
| 26.22 | 21 |
| 27.37 | 26 |
| 27.62 | 25 |
| 28.13 | 20 |

Example 17

Production of Form II Crystal of Maleate

N-{2-Chloro-4-[(6,7-dimethoxy-4-quinolyl)oxy]phenyl}-N'-(5-methyl-3-isoxazolyl)urea (2.0 g) produced in Production Example was added to methanol (27 mL), a solution of maleic acid (1.5 g) in methanol (27 mL) was added dropwise thereto, and the mixture was stirred at room temperature for 4 hr. The resultant precipitate was collected by filtration, and the filtered product was then dried under the reduced pressure. The powder thus obtained was stirred in ethanol (300 mL) under reflux for complete dissolution. The solution was then cooled to 5° C. and was stirred at that temperature overnight. The resultant precipitate was filtered, and the filtered product was then dried under the reduced pressure to give a form II crystal of N-{2-chloro-4-[(6,7-dimethoxy-4-quinolyl)oxy]phenyl}-N'-(5-methyl-3-isoxazolyl)urea maleate (1.9 g, yield 76.0%).

The crystal thus obtained was analyzed by the above-described powder X-ray diffractometry, differential scanning calorimetry, and thermogravimetric measurement.

Table 17 shows positions and relative intensities (%) of peaks with a relative intensity of not less than 20% for the crystal.

FIG. 33 shows a differential scanning calorimetrically measured chart for the crystal with an endothermic peak at a temperature around 180° C. FIG. 34 is a thermogravimetrically measured chart for the crystal.

TABLE 17

| Diffraction angle (2θ) | Relative intensity (>20%) |
|---|---|
| 4.33 | 35 |
| 8.70 | 24 |
| 12.19 | 22 |
| 12.70 | 21 |
| 14.72 | 25 |
| 15.88 | 37 |
| 17.36 | 36 |
| 22.70 | 23 |
| 23.06 | 24 |
| 23.22 | 25 |
| 23.55 | 20 |
| 24.06 | 20 |
| 24.63 | 33 |
| 25.65 | 100 |
| 26.06 | 51 |
| 27.20 | 41 |

Example 18

Production of Form III Crystal of Maleate

N-{2-Chloro-4-[(6,7-dimethoxy-4-quinolyl)oxy]phenyl}-N'-(5-methyl-3-isoxazolyl)urea (2.0 g) produced in Production Example was added to methanol (27 mL), a solution of maleic acid (1.5 g) in methanol (27 mL) was added dropwise thereto, and the mixture was stirred at room temperature for 4 hr. The resultant precipitate was collected by filtration, and the filtered product was then dried under the reduced pressure. The powder thus obtained was stirred in N,N-dimethylformamide (10 mL) at 100° C. for complete dissolution. The solution was then cooled to 5° C. and was stirred at that temperature overnight. The resultant precipitate was filtered, and the filtered product was then dried under the reduced pressure to give a form III crystal of N-{2-chloro-4-[(6,7-dimethoxy-4-quinolyl)oxy]phenyl}-N'-(5-methyl-3-isoxazolyl)urea maleate (1.6 g, yield 65.0%).

The crystal thus obtained was analyzed by the above-described powder X-ray diffractometry, differential scanning calorimetry, and thermogravimetric measurement.

Table 18 shows positions and relative intensities (%) of peaks with a relative intensity of not less than 20% for the crystal.

FIG. 35 shows a differential scanning calorimetrically measured chart for the crystal with endothermic peaks at temperatures around 110° C. and 190° C. FIG. 36 is a thermogravimetrically measured chart for the crystal.

TABLE 18

| Diffraction angle (2θ) | Relative intensity (>20%) |
|---|---|
| 6.29 | 36 |
| 8.91 | 91 |
| 12.45 | 50 |
| 14.03 | 100 |
| 16.14 | 24 |
| 17.82 | 54 |
| 19.79 | 48 |
| 20.44 | 35 |
| 21.97 | 67 |
| 23.34 | 34 |
| 23.53 | 44 |
| 23.88 | 35 |
| 24.11 | 27 |
| 24.59 | 32 |
| 24.80 | 37 |
| 24.94 | 39 |
| 25.42 | 45 |
| 25.69 | 52 |
| 26.98 | 34 |
| 27.28 | 37 |
| 27.99 | 39 |
| 28.37 | 30 |
| 28.53 | 27 |

Example 19

Production of Form IV Crystal of Maleate

N-{2-Chloro-4-[(6,7-dimethoxy-4-quinolyl)oxy]phenyl}-N'-(5-methyl-3-isoxazolyl)urea (2.0 g) produced in Production Example was added to methanol (27 mL), a solution of maleic acid (1.5 g) in methanol (27 mL) was added dropwise thereto, and the mixture was stirred at room temperature for 4 hr. The resultant precipitate was collected by filtration, and the filtered product was then dried under the reduced pressure. The powder thus obtained was stirred in N,N-dimethylacetamide (10 mL) at 100° C. for complete dissolution. The solution was then cooled to room temperature. Ethyl acetate (20 mL) was added dropwise thereto, and the mixture was stirred at room temperature overnight. The resultant precipitate was filtered, and the filtered product was then dried under the reduced pressure to give a form IV crystal of N-{2-chloro-4-[(6,7-dimethoxy-4-quinolyl)oxy]phenyl}-N'-(5-methyl-3-isoxazolyl)urea maleate (1.9 g, yield 75.0%).

The crystal thus obtained was analyzed by the above-described powder X-ray diffractometry, differential scanning calorimetry, and thermogravimetric measurement.

Table 19 shows positions and relative intensities (%) of peaks with a relative intensity of not less than 20% for the crystal.

FIG. 37 shows a differential scanning calorimetrically measured chart for the crystal with an endothermic peak at temperatures around 130° C. and 180° C. FIG. 38 is a thermogravimetrically measured chart for the crystal.

TABLE 19

| Diffraction angle (2θ) | Relative intensity (>20%) |
|---|---|
| 3.62 | 34 |
| 10.37 | 22 |
| 10.57 | 33 |
| 13.30 | 45 |
| 14.00 | 25 |
| 15.47 | 100 |
| 16.62 | 32 |
| 17.42 | 23 |
| 19.53 | 27 |
| 19.76 | 37 |
| 21.18 | 40 |
| 21.48 | 43 |
| 24.14 | 23 |
| 24.52 | 36 |
| 24.69 | 39 |
| 25.21 | 85 |
| 25.54 | 63 |
| 25.76 | 59 |
| 26.11 | 47 |
| 26.23 | 41 |
| 26.84 | 46 |
| 27.57 | 42 |
| 27.77 | 39 |
| 27.95 | 30 |

Test Example 1

Stability of Crystal Under Heating (73° C.) Conditions

Form I to III crystals of hydrochloride, form I crystal of nitrate, form I and II crystals of sulfate, form I crystal of methanesulfonate, form I and II crystals of p-toluenesulfonate, and form I and II crystals of maleate of N-{2-chloro-4-[(6,7-dimethoxy-4-quinolyl)oxy]phenyl}-N'-(5-methyl-3-isoxazolyl)urea were stored at 73° C. for 2 weeks. At the end of the 2-week period, for each of the crystals, a powder X-ray diffraction chart was measured by method 1 to evaluate the stability of each crystal under high temperature (73° C.) conditions.

The results were as shown in Table 20 and Table 21.

For the hydrochloride, form III crystal was converted to form II crystal (see Table 20), and for the sulfate, form II crystal was converted to a novel crystalline form (see Table 21). For the other crystals, no change was observed, indicating that these crystals were stable under high temperature conditions.

TABLE 20

| Diffraction angle (2θ) | Relative intensity (>20%) |
|---|---|
| 9.38 | 45 |
| 12.13 | 57 |
| 12.60 | 28 |
| 12.96 | 30 |
| 20.39 | 23 |
| 21.31 | 37 |
| 21.51 | 34 |
| 21.80 | 29 |
| 22.15 | 56 |
| 23.04 | 31 |
| 23.20 | 32 |
| 24.24 | 38 |
| 25.35 | 100 |
| 26.13 | 36 |
| 26.58 | 21 |

TABLE 21

| Diffraction angle (2θ) | Relative intensity (>20%) |
|---|---|
| 6.22 | 25 |
| 8.69 | 26 |
| 9.59 | 24 |
| 12.44 | 49 |
| 13.91 | 70 |
| 14.72 | 40 |
| 15.44 | 80 |
| 17.30 | 33 |
| 17.48 | 31 |
| 21.56 | 31 |
| 21.97 | 100 |
| 22.62 | 37 |
| 25.00 | 48 |
| 25.19 | 43 |
| 26.32 | 47 |
| 26.55 | 24 |
| 27.15 | 30 |
| 29.83 | 24 |

Test Example 2

Stability of Crystal Under High Humidity (40° C., 75% RH) Conditions

Form I to III crystals of hydrochloride, form I crystal of nitrate, form I and II crystals of sulfate, form I crystal of methanesulfonate, form I and II crystals of p-toluenesulfonate, and form I and II crystals of maleate of N-{2-chloro-4-[(6,7-dimethoxy-4-quinolyl)oxy]phenyl}-N'-(5-methyl-3-isoxazolyl)urea were stored under conditions of 40° C. and 75% RH for 2 weeks. At the end of the 2-week period, for each of the crystals, a powder X-ray diffraction chart was measured by method 1 to evaluate the stability of each crystal under high humidity (40° C., 75% RH) conditions.

The results were as shown in Tables 22 to 24.

For the hydrochloride, form III crystal was converted to form I crystal (see Table 22), and for the sulfate, form I crystal was converted to a mixture of form I crystal and a novel crystalline form (see Table 23), and from II crystal was converted to a novel crystalline form (see Table 24). For the other crystals, no change was observed, indicating that these crystals were stable under high humidity conditions.

TABLE 22

| Diffraction angle (2θ) | Relative intensity (>20%) |
|---|---|
| 8.74 | 25 |
| 11.46 | 100 |
| 15.28 | 27 |
| 17.53 | 23 |
| 18.79 | 20 |
| 19.99 | 22 |
| 22.58 | 57 |
| 23.01 | 53 |
| 23.36 | 23 |
| 25.35 | 42 |
| 26.25 | 56 |
| 26.60 | 55 |
| 27.01 | 28 |
| 28.55 | 35 |

TABLE 23

| Diffraction angle (2θ) | Relative intensity (>20%) |
|---|---|
| 9.18 | 54 |
| 9.53 | 34 |
| 10.08 | 24 |
| 12.27 | 33 |
| 13.94 | 33 |
| 14.33 | 23 |
| 14.65 | 30 |
| 15.18 | 100 |
| 17.94 | 23 |
| 18.36 | 24 |
| 21.96 | 42 |
| 22.59 | 22 |
| 22.77 | 25 |
| 23.28 | 22 |
| 23.98 | 21 |
| 24.14 | 21 |
| 26.40 | 23 |

TABLE 24

| Diffraction angle (2θ) | Relative intensity (>20%) |
|---|---|
| 10.20 | 100 |
| 15.27 | 69 |
| 15.65 | 89 |
| 20.73 | 69 |
| 22.61 | 67 |
| 22.79 | 65 |
| 24.52 | 73 |
| 25.04 | 63 |
| 25.21 | 71 |
| 25.57 | 85 |
| 25.69 | 87 |
| 26.18 | 76 |
| 26.46 | 67 |
| 27.52 | 64 |
| 27.39 | 63 |

Test Example 3

Stability of Crystal Against Physical Stress

Each of form I to III crystals of hydrochloride, form I crystal of nitrate, form I and II crystals of sulfate, form I crystal of methanesulfonate, form I and II crystals of p-toluenesulfonate, and form I and II crystals of maleate of N-{2-chloro-4-[(6,7-dimethoxy-4-quinolyl)oxy]phenyl}-N'-(5-methyl-3-isoxazolyl)urea was ground in a mortar. In grinding each crystal in the mortar, about 1 mg of each crystal sample was placed and ground in an agate mortar or a porcelain mortar. For each sample before and after grinding, a powder X-ray diffraction chart was measured by method 1 to evaluate the stability of the crystal against physical stress.

The results were as shown in Tables 25 to 28.

For form III crystal of hydrochloride (Table 25), form I crystal of sulfate (Table 26), form II crystal of sulfate (Table 27), and form I crystal of maleate (Table 28), a lowering in peak intensity in the powder X-ray diffraction was observed. The other crystals remained unchanged, indicating that these crystals were also stable against the physical stress.

TABLE 25

| Diffraction angle (2θ) | Peak intensity (Before grinding) | Peak intensity (After grinding) |
|---|---|---|
| 5.07 | 842 | — |
| 7.20 | 2162 | 1412 |
| 11.42 | 1275 | 751 |
| 14.58 | 880 | — |
| 20.43 | 909 | — |
| 21.86 | 1282 | 1115 |
| 23.75 | 1130 | 1152 |
| 24.59 | 1156 | 1181 |
| 24.71 | 910 | — |
| 25.18 | 1313 | — |
| 25.34 | 1301 | 1437 |
| 26.01 | 1329 | 1254 |

TABLE 26

| Diffraction angle (2θ) | Peak intensity (Before grinding) | Peak intensity (After grinding) |
|---|---|---|
| 8.71 | 1174 | 742 |
| 9.40 | 1320 | 975 |
| 9.56 | 964 | — |
| 12.30 | 1699 | 1400 |
| 13.98 | 1944 | 1213 |
| 14.41 | 1175 | 818 |
| 15.13 | 2045 | 1621 |
| 17.28 | 1097 | 790 |
| 21.40 | 796 | — |
| 21.96 | 2101 | 1642 |
| 25.39 | 844 | 1000 |
| 25.61 | 712 | 724 |
| 26.90 | 728 | 1160 |

TABLE 27

| Diffraction angle (2θ) | Peak intensity (Before grinding) | Peak intensity (After grinding) |
|---|---|---|
| 6.19 | 1829 | 1459 |
| 8.09 | 784 | 676 |
| 12.35 | 1870 | 1368 |
| 13.08 | 804 | 646 |
| 16.65 | 2402 | 1653 |
| 18.38 | 916 | 913 |
| 18.52 | 1086 | 731 |
| 21.12 | 687 | — |
| 22.07 | 1423 | 1638 |
| 22.17 | 1658 | — |
| 23.03 | 945 | — |
| 23.94 | 907 | 863 |
| 24.13 | 825 | 664 |
| 24.78 | 773 | 724 |
| 25.68 | 1008 | 1017 |
| 26.54 | 844 | 736 |
| 27.02 | 801 | — |
| 28.14 | 801 | 746 |

TABLE 28

| Diffraction angle (2θ) | Peak intensity (Before grinding) | Peak intensity (After grinding) |
| --- | --- | --- |
| 6.30 | 1030 | 799 |
| 9.82 | 1320 | 1342 |
| 11.68 | 1437 | 1947 |
| 14.25 | 2239 | 3348 |
| 15.27 | 1621 | 1548 |
| 15.66 | 4597 | 3096 |
| 18.86 | 3864 | 2020 |
| 21.85 | 2281 | 1523 |
| 22.12 | 3568 | 2951 |
| 26.22 | 952 | 1869 |
| 27.37 | 1177 | 1167 |
| 27.62 | 1151 | 978 |
| 28.13 | 931 | 699 |

Test Example 4

Hygroscopicity of Crystal

Form I to III crystals of hydrochloride, form I crystal of nitrate, form I and II crystals of sulfate, form I crystal of methanesulfonate, form I and II crystals of p-toluenesulfonate, and form I and II crystals of maleate of N-{2-chloro-4-[(6,7-dimethoxy-4-quinolyl)oxy]phenyl}-N'-(5-methyl-3-isoxazolyl)urea were stored under conditions of 40° C. and 75% RH for 2 weeks. Before and after the storage, the weight of each crystal was measured to determine a difference in weight between before the storage and after the storage.

For each crystal, the hygroscopicity was evaluated based on the weight change.

The results were as shown in Table 29.

For each of form I and II crystals of hydrochloride, form I and II crystals of p-toluenesulfonate, and form I and II crystals of maleate, the hygroscopicity was found to be on a low level. On the other hand, each of form III crystal of hydrochloride, form I crystal of nitrate, form I crystal of sulfate, and form I crystal of methanesulfonate were found to be highly hygroscopic.

TABLE 29

| Crystalline form of salt | After 2 days | After 1 week | After 2 weeks |
| --- | --- | --- | --- |
| Form I crystal of hydrochloride | 0.00% | 0.01% | 0.00% |
| Form II crystal of hydrochloride | 0.30% | 0.29% | 0.20% |
| Form I crystal of p-toluenesulfonate | 0.29% | 0.24% | 0.25% |
| Form II crystal of p-toluenesulfonate | 0.84% | 0.70% | 0.80% |
| Form I crystal of maleate | 0.46% | 0.41% | 0.53% |
| Form II crystal of maleate | 0.60% | 0.42% | 0.57% |
| Form III crystal of hydrochloride | 1.06% | 1.49% | 1.93% |
| Form I crystal of sulfate | 4.20% | 4.21% | 4.25% |
| Form I crystal of nitrate | 2.04% | 2.22% | 2.22% |
| Form I crystal of methanesulfonate | 2.58% | 2.70% | 2.84% |

The invention claimed is:

1. Crystalline N-{2-chloro-4-[(6,7-dimethoxy-4-quinolyl)oxy]phenyl}-N'-(5-methyl-3-isoxazolyl)urea monohydrochloric acid salt monohydrate.

2. The crystalline compound according to claim 1, wherein in powder X-ray diffractometry, the crystalline compound has peaks with not less than 10% relative intensity at least the following diffraction angles (2θ):

TABLE A-1

| Diffraction angle (2θ) |
| --- |
| 11.47 ± X |
| 22.59 ± X |
| 23.02 ± X |
| 26.27 ± X |
| 26.63 ± X | wherein X is 0 to 0.20.

3. The crystalline compound according to claim 2, wherein the relative intensity in said diffraction angles (2θ) is not less than 15%.

4. The crystalline compound according to claim 2, wherein the relative intensity in said diffraction angles (2θ) is not less than 20%.

5. The crystalline compound according to claim 2, wherein the relative intensity in said diffraction angles (2θ) is not less than 25%.

6. The crystalline compound according to claim 2, wherein the relative intensity in said diffraction angles (2θ) is not less than 30%.

7. The crystalline compound according to any one of claims 2 to 6, wherein X is 0 to 0.10.

8. The crystalline compound according to claim 1, wherein in powder X-ray diffractometry, the crystalline compound has peaks with not less than 10% relative intensity at least the following diffraction angles (2θ):

TABLE B-1

| Diffraction angle (2θ) |
| --- |
| 8.76 ± X |
| 11.47 ± X |
| 15.28 ± X |
| 17.16 ± X |
| 17.53 ± X |
| 18.80 ± X |
| 20.02 ± X |
| 22.59 ± X |
| 23.02 ± X |
| 25.32 ± X |
| 25.43 ± X |
| 26.27 ± X |
| 26.63 ± X |
| 27.00 ± X |
| 28.57 ± X | wherein X is 0 to 0.20.

9. The crystalline compound according to claim 8, wherein the relative intensity in said diffraction angles (2θ) is not less than 15%.

10. The crystalline compound according to claim 8, wherein the relative intensity in said diffraction angles (2θ) is not less than 20%.

11. The crystalline compound according to any one of claims 8 to 10, wherein X is 0 to 0.10.

12. The crystalline compound according to claim 1, wherein in powder X-ray diffractometry, the crystalline compound has the following diffraction angles (2θ) and relative intensities:

TABLE 1

| Diffraction angle (2θ) | Relative intensity |
|---|---|
| 8.76 | 22 |
| 11.47 | 100 |
| 15.28 | 21 |
| 17.16 | 21 |
| 17.53 | 23 |
| 18.80 | 21 |
| 20.02 | 25 |
| 22.59 | 35 |
| 23.02 | 37 |
| 25.32 | 29 |
| 25.43 | 23 |
| 26.27 | 36 |
| 26.63 | 32 |
| 27.00 | 29 |
| 28.57 | 28. |

13. A process for producing a crystal N-{2-chloro-4-[(6,7-dimethoxy-4-quinolyl)oxy]phenyl}-N'-(5-methyl-3-isoxazolyl)urea, monhydrochloric acid salt monohydrate, said process comprising the steps of:
adding hydrochloric acid to a solution of N-{2-chloro-4-[(6,7-dimethoxy-4-quinolyl)oxy]phenyl}-N'-(5-methyl-3-isoxazolyl)urea in an aprotic polar solvent selected from N,N-dimethylformamide and N,N-dimethylacetamide;
adding ethanol and water to the above solution to precipitating crystals from the solution.

14. The process according to claim 13, wherein said hydrochloric acid has a concentration of 10 to 14 N.

15. The process according to claim 13, wherein in powder X-ray diffractometry, the crystal has peaks with not less than 10% relative intensity at least the following diffraction angles (2θ):

TABLE A-1

| Diffraction angle (2θ) |
|---|
| 11.47 ± X |
| 22.59 ± X |
| 23.02 ± X |
| 26.27 ± X |
| 26.63 ± X | wherein X is 0 to 0.20.

16. The process according to claim 14, wherein in powder X-ray diffractometry, the crystal has peaks with not less than 10% relative intensity at least the following diffraction angles (2θ):

TABLE A-1

| Diffraction angle (2θ) |
|---|
| 11.47 ± X |
| 22.59 ± X |
| 23.02 ± X |
| 26.27 ± X |
| 26.63 ± X | wherein X is 0 to 0.20.

* * * * *

UNITED STATES PATENT AND TRADEMARK OFFICE

(12)       CERTIFICATE EXTENDING PATENT TERM
UNDER 35 U.S.C. 156

(68) PATENT NO. : 7,166,722

(45) ISSUED : January 23, 2007

(75) INVENTOR : MATSUNAGA, Naoki; YOSHIDA, Satoshi; YOSHINO, Ayako; and NAKAJIMA, Tatsuo

(73) PATENT OWNER : Kyowa Kirin Co., Ltd.

(95) PRODUCT : FOTIVDA® (tivozanib)

This is to certify that an application under 35 U.S.C. 156 has been filed in the United States Patent and Trademark Office, requesting extension of the term of U.S. Patent No. 7,166,722 based upon the regulatory review of the product FOTIVDA® (tivozanib) by the Food and Drug Administration. According to United States Patent and Trademark Office records, the original expiration date of the patent as of the date of issuance of this certificate is November 16, 2023. Because it appears that the requirements of the law have been met, this certificate extends the term of the patent for the period of

(94)                                                                              five years subject to the payment of maintenance fees as provided by law, with all rights pertaining thereto as provided by 35 U.S.C. 156.

I have caused the seal of the United States Patent and Trademark Office to be affixed this 4th day of March 2025.

Coke Morgan Stewart
Acting Under Secretary of Commerce for Intellectual Property and Acting Director of the United States Patent and Trademark Office